United States Patent [19]
Cabib

[11] Patent Number: 6,018,587
[45] Date of Patent: Jan. 25, 2000

[54] METHOD FOR REMOTE SENSING ANALYSIS BE DECORRELATION STATISTICAL ANALYSIS AND HARDWARE THEREFOR

[75] Inventor: Dario Cabib, Timrat, Israel

[73] Assignee: Applied Spectral Imaging Ltd., Migdal Haemek, Israel

[21] Appl. No.: 08/886,293

[22] Filed: Jul. 1, 1997

Related U.S. Application Data

[62] Continuation-in-part of application No. 08/759,342, Dec. 2, 1996, Pat. No. 5,719,024, which is a continuation-in-part of application No. 08/718,831, Sep. 24, 1996, abandoned, which is a continuation-in-part of application No. 08/635, 820, Apr. 22, 1996, Pat. No. 5,817,462, which is a continuation-in-part of application No. 08/575,191, Dec. 20, 1995, Pat. No. 5,936,731, which is a continuation-in-part of application No. 08/571,047, Dec. 12, 1995, Pat. No. 5,784,162, which is a continuation-in-part of application No. 08/392, 019, Feb. 21, 1995, Pat. No. 5,539,517, which is a continuation-in-part of application No. 08/107,673, filed as application No. PCT/US92/01171, Feb. 19, 1992, abandoned.

[30] Foreign Application Priority Data

Feb. 21, 1991 [IL] Israel ................................ 97328
Feb. 19, 1992 [WO] WIPO ..................... PCT/US92/01171

[51] Int. Cl.$^7$ ..................................................... G06K 9/62
[52] U.S. Cl. .......................... 382/165; 382/209; 382/224
[58] Field of Search .......................... 435/6; 364/724.11; 708/314; 382/165, 191, 209, 217, 218, 224, 129

[56] References Cited

U.S. PATENT DOCUMENTS

| | | | |
|---|---|---|---|
| 4,025,772 | 5/1977 | Constant ................................. | 235/156 |
| 4,418,393 | 11/1983 | Zscheile, Jr. ............................ | 364/724 |
| 4,839,843 | 6/1989 | Veldhuis .............................. | 364/724.11 |
| 4,906,940 | 3/1990 | Greene et al. ............................ | 382/16 |
| 5,287,272 | 2/1994 | Rutenburg et al. ................. | 364/413.01 |
| 5,719,024 | 2/1998 | Cabib et al. .................................. | 435/6 |
| 5,729,471 | 3/1998 | Jain et al. ............................ | 364/514 A |
| 5,745,126 | 4/1998 | Jain et al. ............................... | 345/952 |
| 5,834,203 | 11/1998 | Katzir et al. ................................ | 435/6 |

OTHER PUBLICATIONS

Rinker, J.N., "Remote Sensing Tutorial—Multiband, Multispectral and Hyper spectral", U.S. Army Topographic Engineering Center, Fort Belvoir, Va. 22060–5546.

Picchiotti et al, "Multitemporal Principal Component Analysis of Spectral and Spatial Features of the Venice Lagoon", *Int. J. Remote Sensing*, 18(1): 183–196 (1997).

Braude et al, "Satellite Remote Sensing of Waste Water Reservoirs", *Int. J. Remote Sensing*, 16(16): 3087–3114 (1995).

*Primary Examiner*—Andrew W. Johns
*Attorney, Agent, or Firm*—Mark M. Friedman

[57] ABSTRACT

A method for remote scenes classification comprising the steps of (a) preparing a reference template for classification of the remote scenes via (i) classifying a set of reference scenes via a conventional classification technique for obtaining a set of preclassified reference scenes; (ii) using a first spectral imager for measuring a spectral cube of the preclassified reference scenes; (iii) employing a principal component analysis for extracting the spectral cube for decorrelated spectral data characterizing the reference scenes; and (vi) using at least a part of the decorrelated spectral data for the preparation of the reference template for remote scenes classification; (b) using a second spectral imager for measuring a spectral cube of analyzed remote scenes, such that a spectrum of each pixel in the remote scenes is obtained; (c) employing a decorrelation statistical method for extracting decorrelated spectral data characterizing the pixels; and (d) comparing at least a part of the decorrelated spectral data extracted from the pixels of the remote scenes with the reference template.

36 Claims, 16 Drawing Sheets

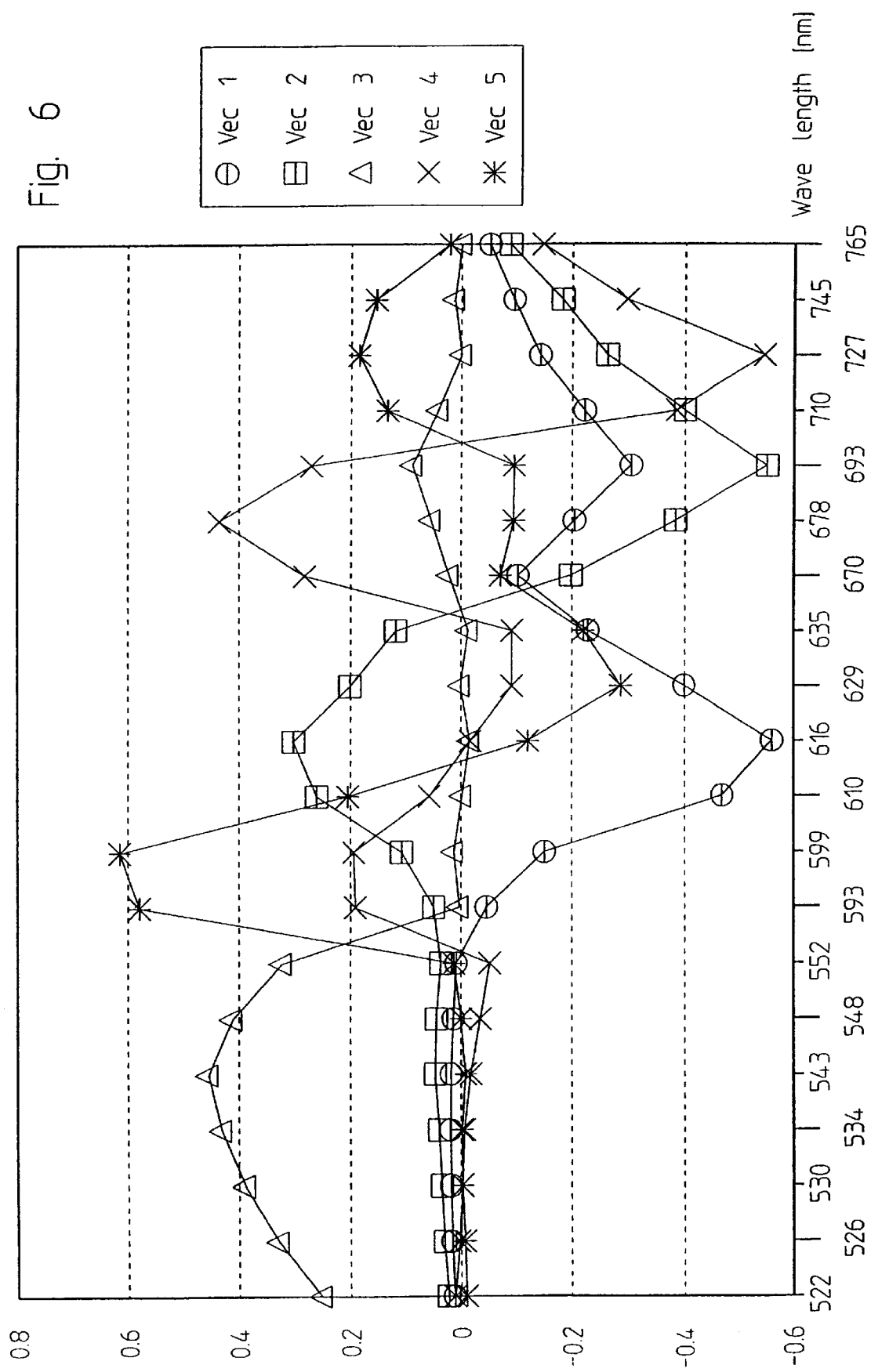

METHOD FOR REMOTE SENSING ANALYSIS BE DECORRELATION STATISTICAL ANALYSIS AND HARDWARE THEREFOR

This is a continuation-in-part of U.S. patent application Ser. No. 08/759,342, filed Dec. 2, 1996, now U.S. Pat. No. 5,719,024, which is a continuation-in-part of U.S. patent application Ser. No. 08/718,831, filed Sep. 24, 1996, now abandoned, which is a continuation-in-part of U.S. patent application Ser. No. 08/635,820, filed Apr. 22, 1996, now U.S. Pat. No. 5,817,462, which is a continuation-in-part of U.S. patent application Ser. No. 08/575,191, filed Dec. 20, 1995, now U.S. Pat. No. 5,936,731 which is a continuation-in-part of U.S. patent application Ser. No. 08/571,047, filed Dec. 12, 1995, now U.S. Pat. No. 5,784,162, which is a continuation-in-part of U.S. patent application Ser. No. 08/392,019 filed Feb. 21, 1995, now U.S. Pat. No. 5,539,517, which is a continuation-in-part of U.S. patent application Ser. No. 08/107,673, filed Aug. 18, 1993, now abandoned which was filed as PCT/US92/01171 on Feb. 7, 1992.

FIELD AND BACKGROUND OF THE INVENTION

The present invention relates to remote sensing. More particularly, the present invention relates to a method for classification of remote scenes by decorrelation statistical analysis of spectra systematically derived from the scenes. The invention further relates to hardware for such classification, the hardware is dedicated or tunable according to parameters derived from the decorrelation statistical analysis.

A thorough tutorial concerning the evolution, methods, strategies, devices and applications of remote sensing is given in J. N. Rinker "Remote Sensing Tutorial— Multiband, Multispectral and Hyper spectral" U.S. Army Topographic Engineering Center, Fort Belvoir, Va. 22060-5546, USA, which is incorporated by reference as if fully set forth herein. The following background reconstructs the highlights of this publication.

From the standpoint of image analysis, an image provides two sources of information. One is shape, and the other is intensity of tones and colors. The analysis of shape is a manual procedure and is still the state-of-the-art for getting terrain information about physical properties and conditions in relation to engineering applications such as site selection and evaluation, and to military applications such as cross-country movement. The second source of information is the analysis and evaluation of the colors, tones, and their intensities associated with a given pattern element. Although analysis of these characteristics can be done to some extent by a manual, or "eyeball" evaluation, it is here that digital analysis and computer techniques take over.

The need to get information by observation from afar is old. The techniques employed are very diverse, ranging from watching events from a hill, to probing the depths of space with the latest in technology. The workhorse for obtaining terrain information is electromagnetic radiation, be it reflected, emitted, or luminesced. Such radiation comes from natural sources, such as the sun, as well as from man-made sources. How it is measured is of equal diversity and includes sensors such as the eye, photographic emulsions, photo cells, antennae, charge coupled devices, thermistors, etc. Most often, the results from remote collection systems are presented as an image, or an assembly of images, wherein each image portrays the terrain in a different part of the electromagnetic spectrum.

Reliable, detailed information about the landscape in terms of composition, structure, properties, conditions, and use, are fundamental factors needed for predicting terrain characteristics for engineering site selection and evaluation locating engineering materials, environmental impact and response to stress, cross-country movement, and selecting potential ground water sites and subsurface waste disposal sites, to name but a few. The determination of these factors is based on the manual, or "eyeball", evaluation of shape patterns, especially three-dimensional or stereoscopic shapes, such as landform and drainage, augmented by an evaluation of the patterns of vegetation, cultural development, lineations, and tone and texture. Although information can be derived from monoscopic imagery, there are severe limitations to its quality and quantity. For obtaining this type of terrain information, the manual analysis of stereo imagery is still state-of-the-art (Rinker, J. N., and P. A, Corl 1984: Air photo analysis, photo interpretation logic, and feature extraction. U.S. Army Engineer Topographic Laboratories Report, ETL-0329, Fort Belvior, Va. 22060-5546; Rinker, J. N., and P. A, Corl 1989: An analysis of air photo and radar imagery of Barro Colorado Island, Paname. U.S. Army Engineer Topographic Laboratories Report, ETL-0540, Fort Belvior, Va. 22060-5546;). Digital analysis contributes little. Digital techniques such as band combinations, enhancement, etc., can, however, improve pattern boundaries for visual observation.

Targeting refers to the detection and, hopefully, the identification of specific features, items, or conditions. For success, the target must have some characteristic that differs from its background and which cannot be confused with any other feature in the field of view. For point targets, this is seldom the case. The prediction of detectability is based on physics, and more often than not, this can be dealt with. But, more often than not, identification is iffy, mostly because of signals that, in the spectral band of use, look like the target. For passive systems such as thermal infrared and thermal microwave, these issues are more complex than for the active systems. In general, the more cluttered the scene, for any type of sensor, the more difficult the identification of point source targets. Detection based on shape, size, and arrangement, includes examples such as roads, airports, dams, vehicles, crop/field patterns, structures, and urban areas, and such are usually easier to identify by manual analysis. In addition to shape, differences can also be based in color, spectral reflectance, spectral emittance (temperature), luminescence, acoustical reflectance and emittance, magnetic fields, etc. Application examples include road type (asphalt or cement concrete), diseased vegetation, stressed vegetation, flood boundaries, wetland areas, thermal springs, thermal plumes for power plants, oil slicks, hot spots in burned areas, alteration zones, number of lakes in a region, camouflaged sites, and military units and equipment. Included in targeting are the applications of change detection and monitoring, e.g., seasonal changes in wetlands, desertification, alteration of land use, forest clearing, extent of pack ice etc. Although aerial photography and multiband images are used in these tasks, it is here that computer assisted techniques and digital analysis become important.

For targeting, military or civil, the basic premise is that the more bands one uses to examine the scene, the chances for detection and identification increase. A camouflaged target may resemble the terrain visually, photographically, and thermally, but show a mismatch in the radar bands; or, match in the radio frequencies, but not in the thermal infrared; or match in radar and thermal infrared, but show a mismatch in its solar spectral signature.

Research and development for improving remote sensing capabilities concentrates on two aspects-data analysis and data collection. With reference to data analysis, the field has gone from dependence on manual analysis, or "eyeball" evaluation of image patterns, to the interweaving of spectral data and computer techniques, and, in some cases to the extent of automated procedures. With reference to data collection, the trend has been towards more, as well as narrower spectral bands. The rationale is support of this evolution is the fact that the finer the slice of spectral data, and the more bands that are used, the greater the ability to establish identities and conditions.

In the 1860s, James Clerk Maxwell developed his famous set of four relatively simple equations that established the relations between electricity and magnetism under all conditions, and which combined electricity, magnetism, and light into a single concept. These equations showed that it was no longer possible to consider an electric field and a magnetic field as separate and isolated components. These two fields will always be present together, at mutual right angles-coalesced into an entity known as electromagnetic field, with the electric field associated with voltage, and the magnetic filed associated with current. A changing electric filed induces changes in the magnetic field, which, in turn, induces changes in the electric field, which in turn induces changes in the magnetic field. and on and on as the field propagates outward in all directions-playing leapfrog to infinity. This alternation, which starts at the leading edge of the pulse. can take place only so fast, no more and no less a defining rate at which each field can produce the other. It is this that establishes the speed of travel, and why it is a constant—a constant known as the speed of light in empty space, i.e., a vacuum. A feature of Maxwell's equations, which astounded physicists at the time, was the fact that the speed of propagation predicted by the equations for an electromagnetic field was same value as the speed of light, which had already been measured.

This spread of frequencies is known as the electromagnetic (EM) spectrum, and locations within it can be specified by numbers for frequency (cycles per second) and wavelength (Angstroms, nanometers, micra, feet, miles, etc.), or by words. Words that designate frequency locations are radio terms such as Low Frequency (LF), High Frequency (HF), Very High Frequency (VHF), Ultra High Frequency (UHF), and Extraordinary High Frequency (EHF), at which point they ran out of superlatives. On the wavelength side, amateur radio operators use the terms, 1 meter band, 10 meter band, etc. General descriptors for various portions of the EM spectrum, going from high frequency to low, or from short wavelengths to long, include: gamma ray, x-ray, ultraviolet, visible, infrared, microwave, and radio. The visible part of the EM spectrum covers the approximate wavelength range of 400–700 nanometers (nm). It is not a sharp cutotT at the long wavelength end, and many people can perceive photons with wavelengths well beyond 700 nm. The 400–500 nm band is called blue, the 500–600 nm band green, and the 600–700 nm band red. Wavelengths shorter than 400 nm fall in the ultraviolet region, and wavelengths longer than 700 nm are in the infrared domain, which extends out to a wavelength of 1 mm. Beyond this is the microwave region.

When electromagnetic energy falls on a material, be it gas, liquid, or solid, several things can happen. What happens depends on the electrical properties of the materials, i.e., the index of refraction, or dielectric constant. In turn, this is a function of the oscillation frequency of the incoming electric field. More exactly, what happens depends on changes in the electrical properties between the medium the radiation it is in, and the medium it is entering. If, in going from one medium to another, the radiation encounters a change in electrical properties that takes place in a distance less than its characteristic wavelength, then something must happen to that radiation—it cannot continue as it was. It will undergo, singly or in combination, reflection (scattering), refraction, or absorption.

Because all materials reflect, absorb, or emit photons in ways characteristic of their molecular makeup, a high resolution trace of the intensity of the transmitted, reflected, emitted, or luminesced radiation versus wavelength forms a graphical record unique to a given material. Different materials cannot have identical wave shapes of reflectance, emittance, and luminescence. These characteristic absorption and emittance bands occur in narrow wavelength ranges, 10 mm or less, frequently much less; and, unless the instruments have that kind of spectral resolution, these details cannot be recorded. Many laboratory and field instruments have the needed spectral resolution, but only recently has such capability entered the domain of airborne and space remote sensing. Basically, remote sensing is the task of counting and recording photons in terms of intensity versus wavelength, phase, and polarization—photons associated with reflectance, emittance, and luminescence.

The recording of the reflected component of radiation is the most common form of remote sensing, and can involve the sun, lasers, and radio frequencies. The sun is the most frequently used source, and in the reflected solar spectrum (0.4–2.5 micra), supports sensors such as cameras, the Landsat Multispectral Scanner (MSS) and Thematic Mapper (TM) bands 1, 2, 3, 4, 5, and 7 (band 6 being a thermal infrared band), SPOT, and the hyperspectral systems such as the Airborne Visible Infrared Imaging Spectrometer (AVIRIS). The tone differences that define boundaries of shapes, soil changes, and the highlight and shadow tones are due to different amounts of radiation reflected to the sensor from the various surfaces.

The amount of radiation reflected from a surface depends on the wavelength band being used, its angle of incidence with the surface, the orientation of the sensor in relation to the surface and the illuminant, the material's molecular composition, and the surface structure. Molecular composition, however, sets the stage, and as we progress to remote sensors that record reflected energy in narrower and narrower bands, we become more interested in the details of the interaction of electromagnetic energy with matter.

A surface that reflects uniformly across the visible and photographic parts of the EM spectrum, is called a neutral surface—i.e., it does not treat any one wavelength different from any other. For normal angles of illumination no neutral material is a perfect reflector, i.e., 100% reflectance throughout the spectrum. Nor is it a perfect absorber, i.e., 0% reflectance. If it has a high reflectance, it is called white. If it has a low reflectance, it is called black. In between it is called gray.

Most materials reflect more photons of some wavelengths than of other wavelengths, e.g., a blue surface reflects blue light, and absorbs green and red, a yellow surface absorbs blue, and reflects green and red, whereas a green surface reflects green light, but absorbs blue and red. If three surfaces, e.g., blue, green, and red, reflect the same amount of photons—i.e., the intensity from the blue surface is the same as the green, which is the same as the red—then a black and white photograph would show them as the same gray tone—they would be indistinguishable. A normal color film, however, like the eye, is a multiband system. It has three bands, or channels, that separately document the intensities in the blue, green, and red bands, and displays the results as a color composite—showing that there are three different objects in the scene.

In the visible part of the spectrum, healthy vegetation absorbs blue light, reflects some of the photons in the green band, and absorbs photons in the red band—thus, we see healthy leafy vegetal material as green, and it would be recorded as such in a normal color film. Healthy leafy vegetation is much more reflective in the infrared part of the spectrum, than in the visible; which is why, in black and white infrared photography, most vegetation shows as very bright tones. Vegetation stress may be detected at the 1.4 and 1.9 micra regions which reflect water absorption. As a plant loses water, these bands become shallower, and thereby provide another indicator of vegetation stress.

The infrared brightness of healthy vegetation is a useful characteristic for military targeting. In WW II, Eastman Kodak was asked to develop a film that could separate green painted camouflaged targets from the green surrounds of vegetal material. It turns out that, though a visual match, green paint is much less reflective in the infrared, than is vegetation. At that time, color films, such as Kodachrome, were sensitive primarily to photons in the visible part of the spectrum. By extending the sensitivity of one of the three emulsion layers in Ektachrome film out to about 900 nm in the infrared region, Eastman Kodak developed the needed film, which was known as Camouflage Detection film, or CD film. With the proper filter, this film would portray green paint as green, and healthy vegetation as red. The emulsion that had the extended sensitivity was the one sensitive to bluelight, and which was coupled to the cyan dye. Increasing its sensitivity to infrared, out to 900 nm, greatly increased its sensitivity to the more energetic photons at double the frequency, or half the wavelength, i.e., 400–450 nm.

In fact, the emulsion was about ten times more sensitive to blue light than to infrared. Thus, in order to tell which photons, blue or infrared, were responsible for the red tone, a yellow filter was required to prevent blue light from entering the emulsion. In addition to infrared, such a filter passes two thirds of the visible spectra, i.e., green and red, which causes the visual sensation we call yellow. Because the filter rejects the blue third, it is also called a minus-blue filter. Examples include Wratten 11, 12, and 13. With the blue light eliminated, the red response could be attributed to the vegetation—and any green painted object stuck out in stark contrast as green. Because the colors in an infrared photograph are not colors that eyes see in the scene, such a photograph is also called a false color image.

One response of stressed vegetation is loss of the bright infrared reflectance. The stress can be induced by drought, flooding, chemical sprays, senescence, by biological infections such as the rust and wilt, or by infestations such as gypsy moths. In all instances the loss of infrared reflectance provides the basis for detecting the presence of the stress, mapping its extent, and monitoring an area for change. On the military side, camouflage was, and still is, frequently made by cutting branches of trees to lay over the site—and this is effective, but only for a relatively short time. One response of the cut branch is that the leafy material loses its infrared reflectance faster than it loses its green reflectance. Even though looking equally green to the eye, the CD film shows the reflectance loss of the damaged vegetation as dark tones of red/green and green.

After WW II, CD film was evaluated for applications in geology, forestry, wetlands, land use mapping, and for detecting stressed vegetation. It became so useful that the consumer market constantly increased. Eastman Kodak improved the film, and changed its name to Ektachrome Infrared film (EIR).

Normal color film has three spectral bands, or recording channels, i.e., blue, green, and red, which are analogous to bands 1, 2 and 3 of the Landsat Thematic Mapper. The color combines the three channels into a normal color image—a color composite. Adding infrared sensitivity makes four channels—blue, green, red, and infrared-analogous to Landsat TM bands 1, 2, 3 and 4. Taking the photograph through a yellow filter, eliminates channel 1, the blue band, and the final colors in the image result from mixes of intensities in the green, red, and infrared bands. With Landsat TM, the selection is made electronically. Of the seven bands available, one can select band 2, 3 and 4, couple them to blue, green, and red guns and create a false color composite image that is similar to the image from the EIR film with a yellow filter.

In general, the reflectance of earth materials increases as one goes to longer wavelengths. In the ultraviolet, most surfaces have a similar low reflectance. This is why photographs taken in ultraviolet, and in blue light tend to be flat—there is little contrast. Reflectance steadily increases going from blue, to green, to red, and to infrared. It is in the infrared region that brightness, contrast, and other interesting spectral features begin to develop. The reflectance characteristics of playa surface materials, such as calcite, halite, montmorillonite, kaolinite and gypsum have common absorption bands. Strong water absorption bands at 1400 nm and 1900 nm are apparent for some of the materials. For atmospheric water vapor, these broad bands do not represent a single absorption, but a collection of narrower bands. In the 1400 nm region, free water has several absorption bands, including ones at 1350 nm, 1380 nm, and 1460 nm. Unless the spectrometer has a narrow spectral bandpass, these closely adjacent bands cannot be resolved—they blend into one larger band. The 1400 nm band for gypsum shows structure within it that suggest the presence of other bands. A record that shows both bands, i.e., 1400 nm and 1900 nm, indicates undissociated water such as water of hydration, or water trapped in the lattice. Molecular water, which is an important component in gypsum, has other absorption bands known as overtones and combinatorial tones.

Although the molecular make-up of a material establishes the absorption characteristics, the reflected component can be greatly affected by other factors, an important one being surface structure. Surface structure can be defined in terms of wavelength of the radiation concerned. For a surface to be considered a high quality reflector, or mirror, it must be flat to within about a quarter of a wavelength of the radiation to be used. Under this condition, the bulk of the incoming radiation is reflected at an angle that equals the angle of incidence. This is called specular reflection. If the topographic variations of the surface exceed this, then proportionally more of the energy is scattered in other directions, i.e., the diffuse component gets smaller. For remote sensors using reflected sunlight, the radiation wavelengths fall between 400 nm and 2500 nm, or between 0.4 and 2.5 micra. Aside from water, most surfaces have relief variations in excess of this, and are diffuse scatters, e.g., leaves, bark, soil, rocks, concrete, etc. Consequently, when viewing terrain from some point in space, the image tones can vary, even be reversed, as a function of viewing angle in relation to the sun. Looking in the up-sun direction, the sensor receives both the diffuse and specular reflection components. Downsun, the sensor receives diffuse minus specular, i.e., only the backscatter. If the surface variations have an orderly structure, the image patterns are influenced by sun azimuth as well. For example, the ridges and furrows of a freshly plowed field have relief on the order of 15 to 20 cm. Furthermore, it is an ordered relief, i.e., a pattern of parallel lines. If the SuII's rays are parallel to the ridge pattern, the surface receive about the same amount of illumination and the image of the field would have an overall uniform tone. If the sun's rays are perpendicular to the ridge pattern, the field shows as a parallel series of highlights and shadows. X- and C-band radars would show a similar display. For P-band radar (100 cm wavelength), however, the plowed field would be a speculum, or mirror, and would be a dark area, an area of no return, or radar loss, from any angle of illumination.

Radiation absorbed by a material leads to other effects. For one, absorbed photons increase the internal energy, or temperature, of the material, which, in turn, increases the quantity and alters the wavelength distribution of the thermally emitted radiation, both infrared and microwave. This is the most common outcome of absorption, and is the basis for thermal, or passive, remote sensing in either the infrared or the microwave domain. During daylight hours, absorbed sunlight heats the terrain. During the night the terrain cools by radiating into space, and would continue to cool except that the sun comes up and renews the heating cycle.

Thermal infrared techniques are associated with two wavelength regions for which the atmosphere is transparent, i.e., atmospheric windows. These are the 3.5–5.5 and 8–14 micra bands. Although thermal techniques are considered by many to be outside the hyperspectral domain, we include them for practical reasons. First, characteristics of thermal images and the events that influence them, are so different from images formed with reflected radiation that they deserve special mention. Second, terrain analysts in DoD, must be able to provide information from any imagery source. Third, thermal systems provide a different type of image, which is important for targeting. Fourth, these systems are available, and being used. Examples include the Landsat TM band 6 (10.4–12.5 micra wavelength), and the Thermal Infrared Mapping system (TIMS), which has six bands in the 8–14 micra range.

At temperature above absolute zero (0° K. or 273° C.), all matter emits electromagnetic energy. If hot enough, such as a hot stovepipe, a tungsten light bulb, or the sun, the object emits enough energy to effect the eye, or photographic emulsion. At normal earth surface temperatures (-50° to +50° C.), however, the amount of energy emitted is below the threshold level of either a photographic emulsion, or the eye. To detect such low levels of photons, special materials are not only sensitive to infrared radiation, but which have some property, such as electrical resistance, that changes rapidly and significantly with variations in intensity of the incoming radiation. This signal is amplified, displayed on a cathode ray tube and recorded on magnetic tape, or on photographic emulsions via a modulated glow tube, or other device. By convention, the images are printed so that light tones represent warmer surfaces, and dark tones represent cooler surfaces.

The amount of energy emitted from a surface, and its wavelength distribution, depend on temperature. The amount is equal to the fourth power of the absolute temperature multiplied by the emissivity. For a given temperature, the wavelength distribution curve will have a maximum intensity as a specific wavelength known as lambda sub-max ($\lambda$max). As the temperature gets higher, $\lambda$max shifts to shorter wavelength, e.g., at −150° C. it is about 23.2 micra, at 0° C. it is about 10.5 micra, and at 100° C. it is about 7.7 micra. At the sun's temperature, $\lambda$max is about 0.5 micra. Also, as the temperature gets higher, the short wavelength edge of the distribution curve includes higher energy levels, i.e., it goes to shorter wavelengths, and the area under the curve (total energy emitted) gets rapidly larger. Keeping emissivity constant, a warmer body will emit more energy at all wavelengths than will a cooler body, and will incorporate a short wavelength increment denied the cooler material. For normal earth surface temperatures, i.e., −50° C. to 50° C., the wavelength of peak emission is in the 8–14 micra band, which is one of the atmospheric windows. About 40% of the energy is emitted in this band, and about 3% in the 3.0–5.5 micra band. For mapping thermal variations in the terrain the 8–14 micra band is the preferred choice.

Above 250° C., the wavelength of peak emission enters the 3.0–5.5 micra band. For detecting hot targets, this band is the preferred choice. The signal/noise ratio, or the target/background contrast is much greater here. Emissivity, which is wavelength dependent, denotes how good an absorber, or emitter, a material is. Molecules emit energy only at those wavelengths they can absorb. A perfect absorber, or emitter, has an emissivity of 1. A material that absorbs 50% of the incoming radiation, and reflects 50%, has an emissivity of 0.5. So, if two materials have the same physical temperature, but differ in their emissivities, the one with the higher emissivity will emit more energy than the one with the lower, and will be brighter in the image. Many earth materials have emissivities in the 0.7–0.9 range, which means they are fairly good absorbers. This being so, radiation emanating from them is pretty much of surface and near-surface origin. Radiation from molecules at depth is absorbed by molecules above, radiated and absorbed by the next layer, and passed along until there are molecules that can radiate into space. For infrared, the depth of the layer that radiates into space is a fraction of a millimeter. The effective depth of this layer increases with longer wavelengths, being perhaps 2.5 cm in the microwave L-band (23 cm).

This layer is an interface between the material below, and the atmosphere above, and is readily influenced by events on both sides. Below, energy transfer is associated with conduction and, in some cases, diffusion. Above, atmospheric variables take over. These can quickly, and radically, alter the radiation characteristics of the surfaces—eliminating, subduing, or increasing thermal contrast. Thus, thermal contrast is influenced by a variety of diurnal and seasonal variations in climatic and meteorological factors, such as wind, atmospheric pressure, dew, rain, humidity, incoming space radiation, etc. Wind can override subsurface conductive events and imprint its own temperature regime, which can create confusing thermal patterns in the form of wind shadows—i.e., surfaces in the lee can be much warmer, or cooler, than surfaces exposed to the wind.

Objects sticking up into the air take on the temperature characteristics of the air. At nighttime, when the air is warmer than the ground, which is cooling by radiation loss, these objects will appear as hotspots. As the night progresses, the air layer, cooled by contact with the cooler ground, becomes thicker, and sequentially cools taller objects that project up into it. By late night the hotspots disappear, except for the tallest trees, or for natural or artificially maintained heat sources.

Also, cooler air is more dense, and being more dense, it flows downslope to settle in the lows, which show as darker tones in the thermal imagery. Darker tones in the lows can also be caused by moist soil, and can lose heat faster. As a result. cool air drainage into the lows is sometimes mistaken for moist soils.

For detection of voids in the terrain, such as caves, tunnels, crevasses in an icecap, or buried installations, atmospheric pressure changes are critical. First, the interior temperatures are usually fairly constant, and are warmer or cooler than the ground surfaces at some time of the day. Also, infrared cannot penetrate the overburden to reveal the presence of the void. The best time to fly is when the void is exhaling, and the outpouring flow of warm air through various openings brings the temperature of the surrounds to above ambient, and they become detectable—i.e., one detects the openings, not the void. Such an outpouring can occur only when the atmospheric pressure is less than the air pressure in the void. Thus, the time to fly is on a descending pressure front.

A second effect of photon absorption is luminescence. There are materials that can absorb photons of one frequency and emit photons of a lower frequency, i.e., lower energy, without any significant increase in temperature. These materials are said to be luminescent. An example is the emission of visible light from minerals when they are illuminated with "black" light, or ultraviolet radiation. Luminescence is an emission of radiation due to electronic transitions, and there are two kinds—fluorescence, which occurs from an excited single state, and phosphorescence, which results from an excited triple state. A distinction can also be made on the basis of time—i.e., how long does the light last after the excitation energy is turned off? This is called the decay time. In fluorescence, the decay time is very short, ranging from $10^{-9}$ to $10^{-3}$ seconds. For example, the fluorescence decay time of rhodamine B in water is about 2.5 nanoseconds (ns). In phosphorescence, the decay time is longer—sometimes much longer. Calcium sulfide, for example, can continue to glow for several hours after the excitation illumination is turned off.

Luminescent techniques require an energy source to excite, or raise the electrons to higher energy levels, and darkness in order to detect the luminesced photons. The sun meets both of these needs—as does the nighttime use of lasers. The sun does not emit a continuous spectrum, i.e., energy at all wavelengths, or frequencies. Although such is generated in the hot core, electronic absorption by elements and ionized atoms in the cooler envelope greatly reduces the intensities of many of the frequencies. When the sun is examined with a good spectroscope, one finds that there are gaps—many gaps—wherein energy is greatly reduced, or absent. These gaps of darkness are narrow in bandwidth, so narrow they are called lines—specifically, Fraunhofer Lines in honor of their discoverer. The spectral bandwidth of these lines are measured in Angstrom units. The ultraviolet, visible, and near infrared portion of the solar spectrum contain over 30,000 Fraunhofer Lines, or lines of darkness. These lines provide the darkness needed for detection of luminescence, and the sun's radiation provides the excitation energy on the short wavelength side of the lines.

A sensor system that can look at both the sun and the earth's surface with detectors sensitive to energy in these dark lines can detect the presence of luminescence photons from the earth's surface, or target. If, from the target, it detects a certain intensity in a dark line band, it cannot be reflected solar energy because such is not coming from the sun. The fill-in must, therefore, be due to luminesced photons from the target. Such is the function of the Fraunhofer Line Discriminator (FLD).

Such things as temperature and pH can alter the characteristics of the luminesced photons. Some materials that are under constant, or steady-state illumination, give a different luminescence signal after an hour or two, than they do to an instant measurement immediately after excitation. These changes show as an increase in intensity at longer wavelengths of emission and a decrease of the shorter wavelength components. In fact, some molecules show little luminescence when first illuminated, but develop an intense emission after steady-state illumination. These characteristics are usually associated with liquids and are indicative of changes caused by chemical reactions. Also, the recorded emission spectrum can be distorted in the short wavelength region by self-absorption within the solution. Whether or not these factors are of concern to remote sensing of earth surface and targeting materials is moot. Some materials, such as vegetation, have a near surface liquid component, and chemical reactions are taking place—e.g., photosynthesis. Furthermore, these surfaces are receiving steady state illumination from the sun for hours. In laboratory measurements, the illumination. i.e., the excitation mode, is of short duration. Another characteristic of luminescence is that for any specific wavelength of excitation, there is an emission spectra that can take place over a fairly broad wavelength band, and the decay times of the longer wavelengths can be considerably longer than those of the shorter wavelengths. The total is still a very short time. In laboratory experiments, decay time spectra have shown links to material types and conditions. Whether or not such has application in remote sensing remains to be determined.

Because all materials reflect, absorb, or emit photons in ways characteristic of their molecular makeup, a high resolution trace of the intensity of the transmitted, reflected, emitted, or luminesced radiation versus wavelength forms a graphical record unique to a given material. Different materials cannot have identical spectral wave shapes of reflectance, emittance, and luminescence. Many of the characteristic absorption and emission bands occur in narrow wavelength ranges, 10 nm or less; and, unless the instruments have that kind of spectral resolution, these details cannot be recorded. Although many laboratory and field instruments exceed this spectral resolution, airborne systems have only recently entered this domain. From a laboratory point of view, the use of spectral measurements to identify and/or assay components of minerals, pigments, pharmaceutical and other organic and inorganic compounds, is old, established, and reliable. With reference to remote sensing, the reasoning goes that if such could be done from air or space, it would give remote sensing a similar capability.

Photographic emulsions were the earliest of the sensors to document landscape scenes, and human activities. By the late 1800's emulsions went airborne, via balloons and kites, to replace the observer and his notepad for recording terrain characteristics and military items of interest. By WW I, cameras were in airplanes and routinely involved in reconnaissance and targeting. It was recognized early on that if one could sample different wavelength of radiation, and compare them, one would have a better chance ol detecting targets, as well as noting changes in the landscape—a multiband concept, although not called that, was now in place.

The first steps were taken in the late 1940's and the 1950's when the Army, along other groups, divided the photographic portion of the electromagnetic spectrum, 400 to 900 nm, into narrower bandpasses by means of various combinations of photographic emulsions and filters. The goal was to improve techniques for detecting targets and mapping conditions such as camouflage, vegetation type, vegetation stress, soil moisture, flood damage, wetland boundaries, to name a few, and the term multiband photography came into being to describe these efforts. Camouflage Detection film, and its improvement into Ektachrome Infrared film is one example of a successful film/filter combination, or multiband approach which later passed into the digital domain of Landsat as the False Color Composite. The bandpasses were still broad, however, ranging from 60 to 100 nm. Nevertheless, multiband photography had applications to some forms of targeting, and change detection.

Next came the Landsat MSS, which recorded reflected sunlight in four broad bands—two in the visible, each of which is 100 nm wide, and two in the infrared, with one being 100 nm wide and the other 1.1 micra. This was followed by the Landsat TM with six bands in the reflected solar region, and one band in the thermal infrared, with the narrowest band being band 3 at 60 nm. Whatever spectral variations occur in the terrain within any of these bands are average out to arrive at a digital number (DN) representing the brightness for the whole band. Extensions of the multispectral concept into the thermal infrared region of the spectrum include the Advanced Very FIigh Resolution Radiometer (AVHRR), and the airborne TIMS developed by Daedalus enterprises, Inc.

In the early 1980's, a system came forth that greatly altered the existing concepts of multispectral remote sensing with reflected solar energy. This was the Airborne Imaging Spectrometer (AIS) developed by the Jet propulsion Laboratory (JPL). The AIS records reflected solar energy in some 128 channels, or images, within the 1.2–2.4 micra region of the spectrum and with a spectral bandwidth for each channel of less than 10 nm. The AIS evolved into the AVIRIS with some 220 raw data channels, or images, within the 0.4–2.45 micra portion of the spectrum. Resanipling gives 210 spectral bands of radiometrically calibrated data. The instantaneous field of view (IFOV) is 1 milliradian, or about 10 meters at operational altitude. Each image is a record of the intensity of reflected sunlight within a spectral bandwidth of less than 10 nm. After calibrations and corrections have been made, the intensity values of the 210 channels, for any given picture element (pixel), can be called up and sequentially displayed along the wavelength axis, as a spectrophotometric trace, i.e., radiometric intensity versus wavelength. Because of the narrowness of the bands, as well as their multiplicity, these systems are called hyperspectral, to differentiate them from the broad band systems, e.g., MSS, TM, SPOT, etc. Systems are also being developed that can operate in even narrower bands, i.e., the sub-nanometer range, for working with gaseous emissions and absorptions. These are called ultraspectral systems.

As indicated, hyperspectral refers to a multiplicity of recording channels that have relatively narrow bandwidths. Since the advent of the AIS and the AVIRIS, other airborne narrow bandpass systems have been developed, and plans laid for satellite follow-ons. The later include the Shuttle Imaging Spectrophotometer Experiment (SISEX), and the High Resolution Imaging Spectrometer (HIRIS). Details of these systems can be found in a Proceedings Issue of the Society of Photo-Optical instrumentation Engineers (Vane, 1987b).

Because the atmosphere absorbs many wavelength components of the incoming sunlight, as well as of the reflected energy en route to the sensor, corrections are needed for many targets. If one is interested in vegetation, this involved the depth and shapes of water absorption bands. Because water vapor is a component of the atmosphere, the analyst does not know how much of the depth and shape of those water bands is due to atmospheric absorption, and how much is due to vegetation absorption. If corrections can be made to remove the atmospheric component via available models such as LowTran, then the residuum can be attributed to plant water.

The notion has been expressed that this is overload, and that such a multiplicity of bands will lead to data constipation in the collection system, the transmission system, and the data reduction and manipulation systems; and, to ease this, unneeded bands should be eliminated from the collection system. If one thinks of hyperspectral imagery as an extension of Landsat, and plans to use the techniques of band rationing throughout 220 channels—then, as far as the data reduction and data manipulation systems go, constipation is at hand. The important point is that, although such band rationing can be done, one can go to a direct call-up of the spectral reflectance plot for any selected area. Nevertheless, reducing the number of channels is thought to be desirable by a number of agencies. Which ones can be eliminated—which ones are unneeded? If you have a narrowly defined goal, the question is easier to answer. For targeting minerals, the geologist can get by with perhaps 30 to 40 bands. For determining crop quantity and quality, the agriculturist can get by with perhaps 20 bands, only a portion of which overlap the geologists' needs. The army, with its interest in terrain, targeting, and intelligence, has need for information about identities, and properties associated with vegetation, soils, rocks, minerals, and cultural objects including camouflage. Perhaps reduction can be made—perhaps there are bands that have no use for anybody—but, it is too early for declarations.

There is another important benefit to an imaging spectrometer. It provides two domains of information for evaluation-image patterns and spectral patterns. From the standpoint of terrain information in terms of materials identities and conditions, potential for dust generation, location of engineering materials, engineering site selection and evaluation, probable location of ground water., surface waste disposal, etc., the manual analysis of stereo imagery is still state-of-the-art. For example, an area can be covered with a vegetative mantle of grass and trees, and all that the spectral data will show will be reflectance traces of chlorophyll. In stereoscopic viewing, however, the shapes of the landform and drainage can reveal that beneath the vegetal mantle rests a thinly interbedded series of limestones and shales dipping gently to the west, and with unstable colluvial materials on the lower slopes.

At present, imaging spectrometers provide only monoscopic imagery, so there is a reduction in the quantity and quality of information that can be derived on the basis of image pattern shapes; but these shapes are present, and they can make significant direct contributions to an analysis, as well as assist in the valuation of the spectral data. Furthermore, existing routines for combining bands to make color composite images, such as Landsat, or the Coastal Zone color Scanner (CZCS), can be directly applied to hyperspectral data.

In any event, the airborne imaging spectrometers are here, the spaceborne systems are in development, and the hyperspectral concept is sound. The issues to be resolved include: what are these systems suited for?—what are their advantages, disadvantages, and limitations?—and, how well will they work?

Spectral data from imaging spectrometers can be evaluated on the basis of: shape of the overall curve, or portions of it; intensity differences at any selected wavelength range; wavelength location of absorption bands; and, depth and shape of absorption bands. To link these to identities and conditions requires an extensive computer library of field and laboratory measurements of spectral reflectance, luminescence, and emittance throughout the reflected solar, and thermal infrared portions of the spectrum—and the software to make the evaluations and comparisons. TEC has a spectral reflectance/luminescence data base of over 1,000 samples of soils, rocks, vegetation, and man-made materials. Such a library needs excellent documentation, because these measured values change with a variety of factors for any given surface, the molecular makeup determines the basic characteristics of absorption, reflectance luminescence, and emittance. These in turn, are modified by structure of the surface, and its orientation in relation to the sensor and to the illuminating source. For example, maintaining a constant field of view and a constant viewing angle, while measuring spectral reflectance at different sun angles and elevations, can result in variances of plus or minus 10 percent. With reference to structure, vegetation can have smooth, crenelated, or wrinkled leaf surfaces, and the leaves and stems can have many different sizes and be arranged in many different ways. This means different highlight/shadow ratio, different amounts of transmitted and re-reflected infrared energy through the biomass, and different amounts of radiation reflecting up through the vegetation from the soil surface.

For a given mineral composition, the spectral signature of a fine textures soil can differ from that of a coarser textured soil. Then, there are the influences of conditions—a term used to denote such things as age, growth phase, wet, dry, weathered, lichen covered, etc. New leaves have a different spectral signature than older leaves, wet soil is different than the same soil when dry, a wheathered rock surface differs from a fresh surface. In reality, these are different chemical forms, which gets back to the earlier statement that the molecular makeup of a surface establishes the basis of reflectance and absorptance. Keeping the target surface and illumination/sensor angles constant, the spectral signature is further modified by climate, season, and meteorological variations. Changes in incoming short and long wave radiation from space, wind and atmospheric pressure greatly alter radiometric signatures, as well as target/background contrasts in thermal imagery.

Multiplicity of measurements is necessary because there can be significant variation within any given class of targets, especially in field measurements. For example, one can measure 20 creosote bushes that look alike and are about the same size and age. But, the result will likely be 20 slightly different spectra-perhaps plus or minus 10% variance, or more, from a derived norm. The variations are mostly in intensity, not wavelength locations of absorption bands. Although the plants look alike, they are not identical—each has some variance in biomass, structure, openness, etc. these factors alter the characteristics of the energy reflected from the vegetal surfaces, as well as the characteristics of the contributing reflected soil component passing through, or reflected from the canopy.

For current systems and typical target areas, the IFOV (10 meters for AVIRIS) encompasses a mixture of surfaces, and the resulting spectral signature is a composite of individual signatures—which presents another problem in relation to digital analysis of spectra data.

In few cases principal component analysis was employed to reduce data ollected by remote sensing systems. See, for example, C. Bradue, N. Ben Yosef and I. Dor "Satellite remote sensing of waste water reservoirs" Int. J. Remote Sensing, 1995, Vol. 16, No. 16, pp. 3087–3114; and A. Picchiotti, R. Casacchia and R. Salvatori "Multitemporal principal component analysis of spectral and spatial features in the Venice lagoon", Int. J. Remote Sensing, 1997, Vol. 18, No. 1, pp. 183–196, both are incorporated by reference as if fully set forth herein. However, the prior art does not teach the application of a decorrelation statistical analysis to full spectra. In the first reference cited above the remote sensing system employed is the SPOT which measures three wide bands. In the second reference cited above employed are only six spectral bands and the principal component analysis was projected over time and not over spectral data.

The present invention is directed at providing a system (hardware and software) which performs a measurement, with higher sensitivity and at higher speed, and encompassing a much smaller amount of data from the outset. The hardware does not require an interferometer, but only a number (N) of what is herein referred to as "decorrelation matched filters", which are placed in the path of the incoming light beam from the remote scenes to be measured. The filters may be of a fixed nature or tunable (AOTF or LCTF). In the latter case a single tunable filter is used to sequentially mimic the decorrelation matched filters under electronic control.

SUMMARY OF THE INVENTION

According to the present invention there is provided a method and hardware for remote scenes classification by decorrelation statistical analysis.

According to further features in preferred embodiments of the invention described below, provided is a method for preparing a reference template for classification of remote scenes comprising the steps of (a) classifying a set of reference scenes via a conventional classification technique for obtaining a set of preclassified scenes; (b) using a spectral imager for measuring a spectral cube of the preclassified referenced scenes; (c) employing a decorrelation statistical method for extracting the spectral cube for decorrelated spectral data characterizing the reference scenes; and (d) using at least a part of the decorrelated spectral data for the preparation of the reference template for remote scenes classification.

According to still further features in the described preferred embodiments the principal component analysis includes the steps of (a) selecting k spectral slices for the spectral cube of the reference scenes; (b) calculating an average spectrum for each of the reference scenes; (c) stretching each of the average spectra for obtaining a stretched average spectrum for each of the reference scenes; (d) averaging the stretched average spectra for each of the reference scenes, for obtaining an ensemble average spectrum for each of the reference scenes; (e) calculating a k dimension eigen system for the ensemble average spectra and extracting N eigenvectors; (f) using the N eigenvectors for defining an N-dimension vector for each of the reference scenes; and (g) using the N-dimension vectors for preparing the reference template for the remote scenes classification.

According to still further features in the described preferred embodiments the principal component analysis further includes the step of (h) performing a spatial averaging procedure over all spectral slices.

According to still further features in the described preferred embodiments provided is a method for remote scenes classification comprising the steps of (a) preparing a reference template for classification of the remote scenes via (i) classifying a set of reference scenes via a conventional classification technique for obtaining a set of preclassified reference scenes; (ii) using a first spectral imager tor measuring a spectral cube of the preclassified reference scenes; (iii) employing a principal component analysis for extracting the spectral cube for decorrelated spectral data characterizing the reference scenes; and (vi) using at least a part ol the decorrelated spectral data for the preparation of the reference template for remote scenes classification; (b) using a second spectral imager for measuring a spectral cube of analyzed remote scenes, such that a spectrum of each pixel in the remote scenes is obtained; (c) employing a decorrelation statistical method for extracting decorrelated spectral data characterizing the pixels; and (d) comparing at least a part of the decorrelated spectral data extracted from the pixels of the remote scenes with the reference template.

According to still further features in the described preferred embodiments provided is a method for remote scenes classification comprising the steps of (a) preparing a reference template for classification of remote scenes via (i) classifying a set of reference scenes via a conventional classification technique for obtaining a set of preclassified reference scenes; (ii) using a first spectral imager for measuring a spectral cube of the preclassified reference scenes; (iii) employing a decorrelation statistical method for extracting the spectral cube for decorrelated spectral data characterizing the reference scenes; and (iv) using at least a part of the decorrelated spectral data for the preparation of the reference template for the remote scenes classification; (b) using a second spectral imager for measuring a spectral cube of analyzed remote scenes, such that a spectrum of each pixel in the remote scenes is obtained; (c) projecting the spectrum of each of the pixels onto the decorrelated spectral data for obtaining a projected spectrum for each of the pixels; and (d) comparing the projected spectra with the reference template.

According to still further features in the described preferred embodiments provided is a method for remote scenes classification comprising the steps of (a) preparing a reference template for classification of remote scenes via (i) classifying a set of reference scenes via a conventional classification technique for obtaining a set of preclassified reference scenes; (ii) using a first spectral imager for measuring a spectral cube of the preclassified reference scenes; (iii) employing a principal component analysis for extracting the spectral cube for decorrelated spectral data characterizing the reference scenes via (a) selecting k spectral slices for the spectral cube of the reference scenes; (b) calculating an average spectrum for each of the reference scenes; (c) stretching the average spectra for obtaining a stretched average spectrum for each of the reference scenes; (d) averaging the stretched average spectra for each of the reference scenes for obtaining an ensemble average spectrum for each of the reference scenes; (e) calculating a k dimension eigen system for the ensemble average spectra and extracting N eigenvectors; (f) using the N eigenvectors for defining an N-dimension vector for each of the reference scenes; and (g) using the N-dimension vectors for preparing the reference template for the remote scenes classification; (b) using a second spectral imager for measuring a spectral cube of the remote scenes, such that a spectrum of each pixel in the remote scenes is obtained; (c) projecting the spectrum of each of the pixels into the N eigenvectors for obtaining a projected N dimension vector for each of the pixels; and (d) correlating each of the projected N dimension vectors with the reference template.

According to still further features in the described preferred embodiments provided is a method of calculating decorrelation matched filters for remote scenes classification, the decorrelation matched filters being for extracting decorrelated spectral data from the remote scenes, the method comprising the step of (a) obtaining decorrelated spectral data characterizing a set of reference scenes via (i) classifying the set of reference scenes via a conventional classification technique for obtaining a set of preclassified reference scenes; (ii) using a first spectral imager for measuring a spectral cube of the preclassified reference scenes; and (iii) employing a decorrelation statistical method for extracting the spectral cube for decorrelated spectral data characterizing the reference scenes; and (b) mathematically manipulating at least a part of the decorrelated spectral data for obtaining a mathematical description of the decorrelation matched filters.

According to still further features in the described preferred embodiments the decorrelated spectral data is obtained using a principal component analysis, which includes expressing each of the reference scenes by a linear combination of N eigenvectors.

According to still further features in the described preferred embodiments provided is a set of decorrelation matched filters for remote scenes classification, the decorrelation matched filters being for extracting decorrelated spectral data from the remote scenes, the set comprising physical filters having shapes, the shapes following a mathematical description, the mathematical description being obtainable by (a) obtaining decorrelated spectral data characterizing a set of reference scenes via (i) classifying the set of reference scenes via a conventional classification technique for obtaining a set of preclassified reference scenes; (ii) using a first spectral imager for measuring a spectral cube of the preclassified reference scenes; and (iii) employing a decorrelation statistical method for extracting the spectral cube for decorrelated spectral data characterizing the reference scenes; and (b) mathematically manipulating at least a part of the decorrelated spectral data for obtaining the mathematical description of the decorrelation matched filters.

According to still further features in the described preferred embodiments provided is a method of tuning a tunable filter for remote scenes classification, the method renders the tunable filter to mimic a set of decorrelation matched filters, and is for extracting decorrelated spectral data from the remote scenes, the method comprising the steps of (a) obtaining decorrelated spectral data characterizing a set of reference scenes via (i) classifying the set of reference scenes via a conventional classification technique for obtaining a set of preclassified reference scenes; (ii) using a first spectral imager for measuring a spectral cube of the preclassified reference scenes; and (iii) employing a decorrelation statistical method for extracting the spectral cube for decorrelated spectral data characterizing the reference scenes; (b) mathematically manipulating at least a part of the decorrelated spectral data for obtaining a mathematical description describing the set of decorrelation matched filters; and (c) sequentially tuning the tunable filter according to the mathematical description.

According to still further features in the described preferred embodiments the tunable filter is selected from the group consisting of AOTF and LCTF.

According to still further features in the described preferred embodiments provided is a method for remote scenes classification comprising the steps of (a) preparing a reference template for classification of the remote scenes via (i) classifying a set of reference scenes via a conventional classification technique for obtaining a set of preclassified reference scenes; (ii) using a first spectral imager for measuring a spectral cube of the preclassified reference scenes; (iii) employing a decorrelation statistical method for extracting the spectral cube for decorrelated spectral data characterizing the reference scenes; and (iv) using at least a part of the decorrelated spectral data for the preparation of the reference template for the remote scenes classification; (b) calculating a mathematical description of decorrelation matched filters for classification of the remote scenes employing the reference template, the calculation being by mathematically manipulating at least a part of the decorrelated spectral data; (c) using the mathematical description of the decorrelation matched filters for manufacturing the decorrelation matched filters, (d) using the decorrelation matched filters for extracting decorrelated spectral data from each pixel of the remote scenes; and (e) comparing the decorrelated spectral data extracted from each pixel of the remote scenes with the reference template.

According to still further features in the described preferred embodiments provided is a method for remote scenes classification comprising the steps of (a) providing a set of decorrelation matched filters for the remote scenes classification, the decorrelation matched filters being for extracting decorrelated spectral data from the remote scenes, the set including physical filters having shapes, the shapes following a mathematical description, the mathematical description being achieved by (i) preparing a reference template for classification of remote scenes via (a) classifying a set of reference scenes via a conventional classification technique for obtaining a set of preclassified reference scenes; (b) using a first spectral imager for measuring a spectral cube of the preclassified reference scenes; (c) employing a decorrelation statistical method for extracting the spectral cube for decorrelated spectral data characterizing the reference scenes; and (d) using at least a part of the decorrelated spectral data for the preparation of the reference template for the remote scenes classification; and (ii) mathematically manipulating at least a part of the decorrelated spectral data for obtaining the mathematical description of the decorrelation matched filters; (b) using the decorrelation matched filters for extracting decorrelated spectral data from each pixel of the remote scenes; and (c) comparing the decorrelated spectral data extracted from each pixel of the remote scenes with the reference template.

According to still further features in the described preferred embodiments the method further comprising the step of (d) according to the comparison, attributing each pixel an artificial color.

According to still further features in the described preferred embodiments provided is a method for remote scenes classification comprising the steps of (a) providing a tunable filter and tuning information for tuning the tunable filter so as to mimic a set of decorrelation matched filters, the tunable filter being for extracting decorrelated spectral data from the remote scenes, the tuning information being achieved by (i) preparing a reference template for classification of remote scenes via (a) classifying a set of reference scenes via a conventional classification technique for obtaining a set of preclassified reference scenes; (b) using a first spectral imager for measuring a spectral cube of the preclassified reference scenes; (c) employing a decorrelation statistical method for extracting the spectral cube for decorrelated spectral data characterizing the reference scenes; and (d) using at least a part of the decorrelated spectral data for the preparation of the reference template for the remote scenes classification; (ii) mathematically manipulating at least a part of the decorrelated spectral data for obtaining the tuning information, which is a mathematical description describing the set of decorrelation matched filters; and (b) using the information for sequentially tuning the tunable filter for extracting decorrelated spectral data from each pixel of the remote scenes; and (c) comparing the decorrelated spectral data extracted from each pixel of the remote scenes with the reference template.

According to still further features in the described preferred embodiments provided is a spectral decorrelation measurement apparatus for remote scenes classification by extracting decorrelated spectral data from the remote scenes, the apparatus is connected to a telescope used to view the remote scenes, the apparatus comprising (a) a detector; and (b) an optical system for transmitting electromagnetic radiation from the remote scenes onto the detector, the optical system including a set of decorrelating matched filters, the decorrelation matched filters being for extracting decorrelated spectral data from the remote scenes, the filters of the set of decorrelation matched filters having shapes, the shapes following a mathematical description, the mathematical description being calculated by (i) obtaining decorrelated spectral data characterizing a set of reference scenes via (a) classifying the set of reference scenes via a conventional classification technique for obtaining a set of preclassified reference scenes; (b) using a first spectral imager for measuring a spectral cube of the preclassified reference scenes; and (c) employing a decorrelation statistical method for extracting the spectral cube for decorrelated spectral data characterizing the reference scenes; and (ii) mathematically manipulating at least a part of the decorrelated spectral data for obtaining the mathematical description of the decorrelation matched filters.

According to still further features in the described preferred embodiments the optical system further includes a collimating lens for collimating radiation reaching any of the decorrelating matched filters.

According to still further features in the described preferred embodiments the decorrelation matched filters are arranged on a rotatable filter carrying element.

According to still further features in the described preferred embodiments provided is a spectral decorrelation measurement apparatus for remote scenes classification by extracting decorrelated spectral data from the remote scenes, the apparatus is connected to a telescope used to view the remote scenes, the apparatus comprising (a) a detector; and (b) an optical system for transmitting electromagnetic radiation from the remote scenes onto the detector, the optical system including a tunable filter and a tuning device, the tuning device being tor tuning the tunable filter, so that the tunable filter sequentially mimics a set of decorrelating matched filters, the decorrelation matched filters mimicked by the tunable filter being for extracting decorrelated spectral data from the remote scenes the tuning of the tunable filter being calculated according to a mathematical description, the mathematical description being calculated by (i) obtaining decorrelated spectral data characterizing a set of reference scenes via (a) classifying the set of reference scenes via a conventional classification technique for obtaining a set of preclassified reference scenes; (b) using a first spectral imager for measuring a spectral cube of the preclassified reference scenes; and (c) employing a decorrelation statistical method for extracting the spectral cube for the spectral cube for decorrelated spectral data characterizing the reference scenes; and (ii) mathematically manipulating at least a part of the decorrelated spectral data for obtaining the mathematical description of the mimicked decorrelation matched filters.

According to still further features in the described preferred embodiments the spectral imager includes an element selected from the group consisting of a dispersion element, a filter, a tunable filter and an interferometer.

According to still further features in the described preferred embodiments the decorrelation statistical method is selected from the group consisting of principal component analysis, canonical variable analysis and singular value decomposition.

According to still further features in the described preferred embodiments the principal component analysis includes expressing each of the scenes as linear combinations of N eigenvectors.

According to still further features in the described preferred embodiments N is an integer greater than two.

According to still further features in the described preferred embodiments N is an integer greater than two and smaller than eight.

The present invention successfully addresses the shortcomings of the presently known configurations by providing a system (hardware and software) which performs a measurement, with higher sensitivity and at higher speed, and encompassing a much smaller amount of data from the outset. The hardware does not require an interferometer, but only a number (N) of what is herein referred to as "decorrelation matched filters", which are placed in the path of the incoming light beam from the object to be measured. The filters may be of a fixed nature or tunable (AOTF or LCTF). In the latter case a single tunable filter is used to sequentially mimic the decorrelation matched filters under electronic control. The filters are matched to take advantage of the correlations between the spectral data derived from remote scenes for best results which include (i) increased signal to noise ratio due to averaging between the correlated data, and (ii) reduction of the amount of data and measurement time needed at the outset, due to the projection of the spectra onto a decorrelated parameter space. As is described below in detail, the number of filters required to achieve a good measurement is much lower than the number of wavelengths of the original spectral image so that the measurement itself is much shorter.

It is an object of the present invention to provide a method and system for the analysis of remote scenes.

It is another object of the present invention to provide a method and system for quick detection of the nature and composition of remote scenes and remote point targets, both are referred herein as remote scenes.

It is still another object of the present invention to provide a method and system which can accomplish the above objectives invention with high signal to noise ratio and in a short time, by employing decorrelation statistical analysis when implementing the method and when constructing the system.

These and other objectives of the invention are further detailed below.

BRIEF DESCRIPTION OF THE DRAWINGS

The invention herein described, by way of example only, with reference to the accompanying drawings, wherein:

FIG. 6 is a graphic presentation of matrix V shown in Table 4;

DESCRIPTION OF THE PREFERRED EMBODIMENTS

Figure 1:
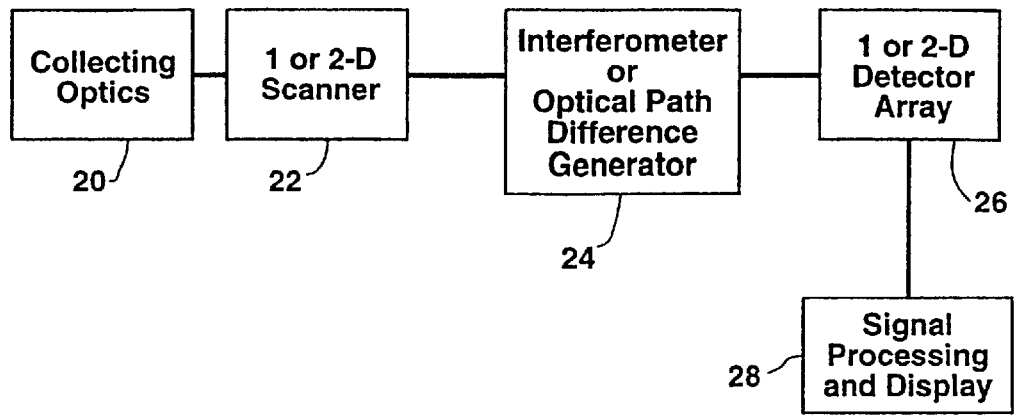
FIG. 1 is a block diagram illustrating the main components of an imaging spectrometer constructed in accordance with U.S. Pat. No. 5,539,517 (prior art)

The present invention is of a method and hardware for remote scenes classification by decorrelation statistical analysis which can be used to provide detailed information about the landscape in terms of composition, structure. properties, conditions, etc. Specifically, the present invention can be used to design decorrelation matched optical filters, also referred herein as "matched" filters, for fast measurement aimed at remote scenes classification.

The term "scene" as used herein refers to any element present in a field of view. Thus a scene may be a corn field, another scene may be a stressed section of that or other field, yet another scene may be a point object, or as such objects are referred to in the art of remote sensing—a target. In other words, the term scene refers to anything which is scented via remote sensing.

The principles and operation of the method and decorrelation matched filters according to the present invention may be better understood with reference to the drawings and accompanying descriptions.

Spectral imaging is the technology that enables the measurement of the spectrum of electronic radiation reflected, emitted, or luminesced by every point (pixel) of a scene. A spectral imager (also referred herein as imaging spectrometer) is an instrument that measures and stores in memory tor later retrieval and analysis the spectrum of radiation reflected, emitted, or luminesced by every point of the scenes which are placed in its field of view. A spectral image is a collection of spectra of the scenes measured by a spectral imager. It is usually organized as an intensity function defined in a three dimensional space in which two dimensions are of an image (x and y), and one is of a spectral axis ($\lambda$). As such, a spectral image is usually referred to as a "cube" of data or "spectral cube".

Prior art teaches different methods of measuring spectral images (i.e., spectral cubes). Devices designed according to these methods include light collection optics; a dispersion element (e.g., a grating). filter(s) (e.g., AOTF or LCTF) or an interferometer; focusing optics; and a two-dimensional array of detectors (typically a CCD in the visible range and other types of detectors in the infrared range, etc.).

The importance of a spectral image measurement resides in the fact that the spectrum of electromagnetic radiation carries information about the composition of matter of which the scenes are made, and therefore it can be used to map and visualize phenomena which cannot be seen otherwise. As a color image is the next step after a black and white image, a spectral image is the next step after a color image. Similarly to the difference of green hues between the leaves of two different types of trees or between a young leaf and an old one, two fluorescent dyes such as Texas Red and Rhodamine appear the same color to the human eye but they are well distinguished by a spectrograph with ten nanometers resolution. Since the colors as perceived by the human eye are composed of combinations of only three colors, red, green and blue (RGB), the number of different regions in a scene that can be classified by color is very limited. For each point of the same scene a spectral imager measures a spectrum which depends on the chemical materials present at that point, and this is a function of wavelength which contains the order of fifty or one hundred data (depending on spectral resolution) instead of only three as for a color image. As a result, small spectral differences or shifts between pixels can be detected by a spectral imager, which the eye would recognize as belonging to the same color class, and therefore many more classes can be distinguished in the scene using a spectral imager, as compared with the human eye.

The present invention is aimed at constructing a system which performs a measurement, with high sensitivity, and at high speed, and encompassing a small amount of data from the outset. The hardware according to the invention does not require an interferometer, but only a number (N) of what is herein referred to as "decorrelation matched filters" (fixed or tunable), which are designed using decorrelating statistical analysis such as principal component analysis (PCA) and are placed in the path of the incoming radiation from the scene to be measured.

It turns out that the number of filters (or their mimicking by a tunable filter) required to achieve a good measurement is much lower than the number of wavelengths of the original spectral image. Furthermore, because there are correlations between the spectral data at different wavelengths, therefore a measurement collected by the hardware according to the invention is much shorter.

The basis for this new concept is the realization that out of flifty data points (or a similar large number) corresponding to fifty wavelengths for a spectrum in a range of Ca. 250 nanometers, there usually are much less than fifty decorrelated data. Decorrelation enables to decrease the amount of data taking at the outset, while the correlations among the data are taken advantage of in order to increase the signal to noise ratio. Thus when the term 'decorrelation' is used herein in the specification and claims below, it refers to an algorithm which defines an initial set of correlated parameters into a new set of parameters which is the linear combination of the initial set, which new set of parameters are independent from each other and are then reduced to a minimal number which still carries the required information.

A classification method based on the position of scenes in a multidimensional space defined by a decorrelated set of parameters is characterized by increased confidence level and shorter measurement time as compared with classification methods employing the initial set of parameters devoid of prior decorrelation.

Each decorrelation matched filter is mathematically described by a weighting function whose shape is such that the parameters which are more correlated are added with a larger weight. Different filters, in order to decorrelate the data, have a different shape and therefore weigh the initial parameters values in different ways. However, the signal obtained using each of the filters has contribution from all initial parameters, therefore the signal is measured with higher signal to noise ratio as compared with other, more conventional, methods.

The decorrelation matched filters are dedicated for a given procedure in which the scenes share features with reference scenes used for obtaining a reference library for the decorrelation analysis.

Nevertheless, should tunable filters such as LCTF and AOTF be used to mimic the set of decorrelation matched filters, appropriate tuning, as is further described hereinbelow, can be used to acquire a mimic of any new set of decorrelation matched filters.

As will be described in greater detail below, in one embodiment of the invention the decorrelation matched filters are placed in a filter wheel of the dedicated hardware according to the invention and are introduced successively in the radiation beam, while a suitable detector builds the images. That is to say that the detector builds an image with one filter, then the wheel rotates to another filter, and the detector builds a new image in synchronization, and so on until one image for each filter has been measured (N images).

As will be further described below, in another embodiment of the invention the decorrelation matched filters are mimicked by a tunable filter such as AOTF or LCTF which are tuned by a tuning device. At successive times the tuning device tunes the tunable filter to mimic one of the N different decorrelation matched filters and the detector builds an image for each of the N mimicked filters.

In both cases, for each pixel in the scenes measured, a vector of dimensionality N is obtained. The elements of this vector are the intensities for that particular pixel, measured through each one of the N filters, and they vary according to the scene reflected by that pixel. Each pixel is then classified as belonging to a particular scene.

FIG. 1 is a block diagram illustrating the main components of a prior art imaging spectrometer disclosed in U.S. Pat. No. 5,539,517, to Cabib et al., which is incorporated by reference as if fully set forth herein. This imaging spectrometer is constructed highly suitable to implement the method of the present invention as it has high spectral (Ca. 4–14 nm depending on wavelength) and spatial (Ca. 30/M $\mu$m where M is the effective fore optics magnification) resolutions.

Thus, the prior art imaging spectrometer of FIG. 1 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scenes to be analyzed. The output of the interferometer is focused onto the detector array 26. Thus, all the required optical phase differences are scanned simultaneously for all the pixels of the scenes in the field of view, in order to obtain all the information required to reconstruct the spectrum for each pixel. The spectra of all the pixels in the field are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, alternative types of interferometers may be employed. These include (1) a moving type interferometer in which the OPD is varied to modulate the light, namely, a Fabry-Perot interferometer with scanned thickness; (2) a Michelson type interferometer which includes a beamsplitter receiving the beam from an optical collection system and a scanner, and splitting the beam into two paths; (3) a Sagnac interferometer optionally combined with other optical means in which interferometer the OPD varies with the angle of incidence of the incoming radiation, such as the four-mirror plus beamsplitter interferometer as further described in the cited U.S. Pat. application (see FIG. 14 there).

Figure 2:
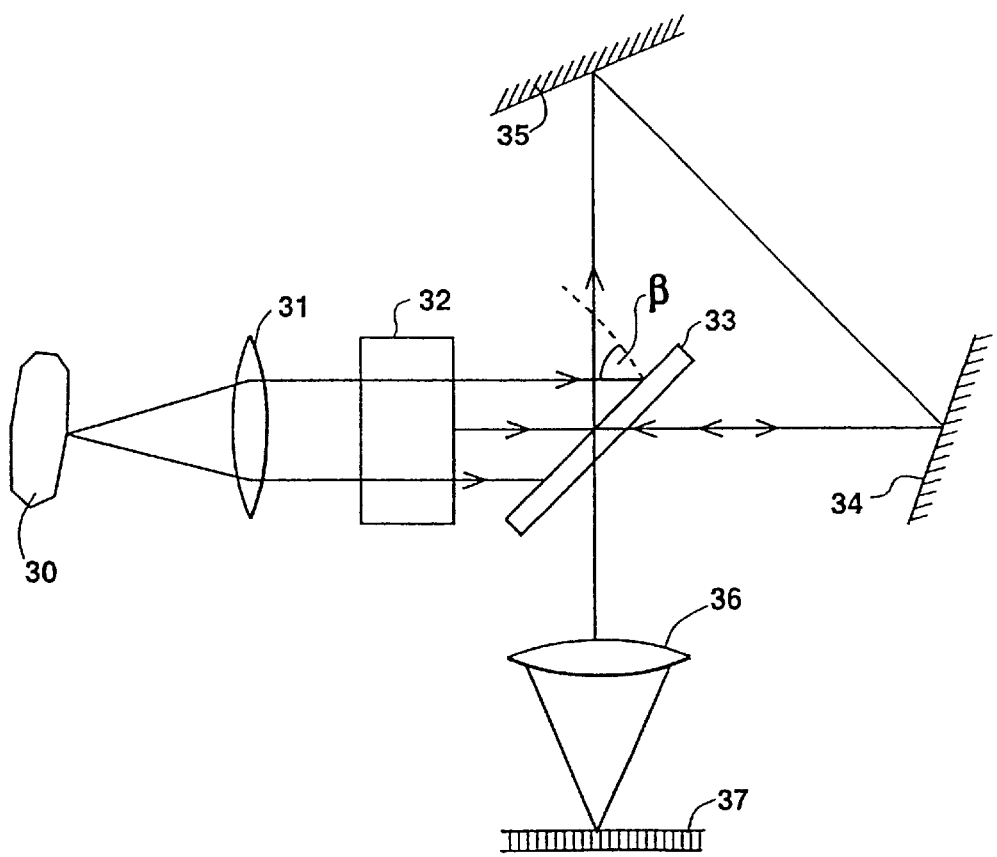
FIG. 2 illustrates a Sagnac interferometer, as used in an imaging spectrometer in accordance with U.S. Pat. No. 5,539,517 (prior art)

FIG. 2 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37. This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 2 the ray which is incident on the beamsplitter at an angle $\beta$ ($\beta=45°$ in FIG. 2) goes through the interferometer with an OPD=0, whereas a ray which is incident at a general angle $\beta-\theta$ undergoes an OPD given by Equation 1:

$$\text{OPD}(\beta,\theta,t,n)=t[(n^2-\sin^2(\beta+\theta))^{0.5}-(n^2-\sin^2(\beta-\theta))^{0.5}+2\sin\beta\sin\theta] \quad (1)$$

where $\beta$ is the angle of incidence of the ray on the beamsplitter; $\theta$ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one can get a double-sided interferogram for every pixel, which helps eliminate phase errors, thereby giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation associated with each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including remote sensing for geological, agricultural and military investigations, and the like.

As mentioned above, an imaging spectrometer in accordance with the invention disclosed in U.S. Pat. No. 5,539,517 was developed by Applied Spectral Imaging Ltd., Industrial Park, Migdal Haemek, Israel and is referred herein as SPECTRACUBE™.

The SPECTRACUBE™ system optically connected to a telescope is used to implement the method of the present invention. The SPECTRACUBE™ system has the following characteristics, listed hereinbelow in Table 1:

TABLE 1

| Character | Performance |
| --- | --- |
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm; 16 nm at 800 nm |
| Acquisition time: | 1.5–50 sec, typical 25 sec |
| FFT processing time: | 20–180 sec, typical 60 sec |

The prior art SPECTRACUBE™ system may be to acquire spectral data of every pixel of scenes in a field of view. However, any spectral imager, i.e., an instrument that measures and stores in memory for later retrieval and analysis the spectrum of radiation associated with every point or pixel of scenes present in its field of view, including filter (e.g., acousto-optic tunable filters (AOTF) or liquid-crystal tunable filter (LCTF)) and dispersive element (e.g., grating) based spectral imagers can be used to acquire the required spectral data. Therefore, it is not intended to limit the scope of the present invention for use of any specific type of spectral imager.

The wavelength range of choice will determine to some extent the exact features of the system. For example, should an interferometric based spectral imager be the choice, then for the spectral range of 300–400 nm the optical components, such as the beam splitter, the optics and the array detector should be made of materials suitable for UV and coated with special UV enhanced coatings, for the spectral range of 400–1,000 nm the optical components, such as the beam splitter, the optics an the array detector should be made of materials suitable for visible radiation and coated with special coatings which optimize the performance in the visible range. The mirrors of the interferometer should be coated for maximum reflection in the various spectral ranges with suitable coatings. The same should be said for the spectral ranges of 1,000–2,000 nm and the infrared ranges 2,000 to 5,000 nm and 8,000 to 15,000 nm. In these last three ranges the array detectors are special detectors based not on Silicon technology but on InSb (Indium Antimonide), HgCdTe (Mercury Cadmium Telluride), and others. One ordinarily skilled in the art would know how to select the suitable components, coatings, etc., to be used in any wavelength range of choice.

Thus, according to the present invention provided is a method and hardware for remote scenes classification by decorrelation statistical analysis which can be used to provide information about the landscape and targets thereon.

First, provided is a method for preparing a reference template for classification of remote scenes. The method includes the steps of (a) classifying a set of reference scenes via a conventional classification technique for obtaining a set of preclassified scenes; a reference scene is a scene of known nature, e.g., soil composition; (b) using a spectral imager for measuring a spectral cube of the preclassified referenced scenes; (c) employing a decorrelation statistical method for extracting the spectral cube for decorrelated spectral data characterizing the reference scenes; and (d) using at least a part of the decorrelated spectral data for the preparation of the reference template for remote scenes classification.

The spectral imager may be of any type. Thus, the spectral imager may include an element selected from the group consisting of a dispersion element, a filter, a tunable filter and an interferometer.

The decorrelation statistical method may be of any type, including, but not limited to, principal component analysis, canonical variable analysis and/or singular value decomposition.

In a preferred embodiment of the invention the principal component analysis includes expressing each of the scenes as linear combinations of N eigenvectors. Preferably, N is an integer greater than two. More preferably, N is an integer greater than two and smaller than eight.

In another preferred embodiment, the principal component analysis includes the steps of (a) selecting k spectral slices for the spectral cube of the reference scenes; (b) calculating an average spectrum for each of the reference scenes; (c) stretching each of the average spectra for obtaining a stretched average spectrum for each of the reference scenes; (d) averaging the stretched average spectra for each of the reference scenes, for obtaining an ensemble average spectrum for each of the reference scenes; (e) calculating a k dimension eigen system for the ensemble average spectra and extracting N eigenvectors; (f) using the N eigenvectors for defining an N-dimension vector for each of the reference scenes; and (g) using the N-dimension vectors for preparing the reference template for the remote scenes classification. k is preferably an integer greater than two, preferably greater than nine.

Preferably the principal component analysis further includes the step of (h) performing a spatial averaging procedure over all spectral slices.

Second, provided is a method for remote scenes classification. The method includes the steps of (a) preparing a reference template for classification of the remote scenes via (i) classifying a set of reference scenes via a conventional classification technique for obtaining a set of preclassitled reference scenes; (ii) using a first spectral imager for measuring a spectral cube of the preclassified reference scenes; (iii) employing a principal component analysis for extracting the spectral cube for decorrelated spectral data characterizing the reference scenes; and (vi) using at least a part of the decorrelated spectral data for the preparation of the reference template for remote scenes classification; (b) using a second spectral imager for measuring a spectral cube of analyzed remote scenes, such that a spectrum of each pixel in the remote scenes is obtained; (c) employing a decorrelation statistical method for extracting decorrelated spectral data characterizing the pixels; and (d) comparing at least a part of the decorrelated spectral data extracted from the pixels of the remote scenes with the reference template.

Third, provided is another method for remote scenes classification. The method includes the steps of (a) preparing a reference template for classification ol remote scenes via (i) classifying a set of reference scenes via a conventional classification technique for obtaining a set of preclassified reference scenes; (ii) using a first spectral imager for measuring a spectral cube of the preclassified reference scenes; (iii) employing a decorrelation statistical method for extracting the spectral cube for decorrelated spectral data characterizing the reference scenes; and (iv) using at least a part of the decorrelated spectral data for the preparation of the reference template for the remote scenes classification; (b) using a second spectral imager for measuring a spectral cube of analyzed remote scenes, such that a spectrum of each pixel in the remote scenes is obtained; (c) projecting the spectrum of each of the pixels onto the decorrelated spectral data for obtaining a projected spectrum for each of the pixels; and (d) comparing the projected spectra with the reference template. Preferably the method further includes the step of (1) according to the comparison, attributing each pixel an artificial color.

Fourth, provided is yet another method for remote scenes classification. The method includes the steps of (a) preparing a reference template for classification of remote scenes via (i) classifying a set of reference scenes via a conventional classification technique for obtaining a set of preclassified reference scenes; (ii) using a first spectral imager for measuring a spectral cube of the preclassified reference scenes; (iii) employing a principal component analysis for extracting the spectral cube for decorrelated spectral data characterizing the reference scenes via (a) selecting k spectral slices for the spectral cube of the reference scenes; (b) calculating an average spectrum for each of the reference scenes; (c) stretching the average spectra for obtaining a stretched average spectrum for each of the reference scenes; (d) averaging the stretched average spectra for each of the reference scenes for obtaining an ensemble average spectrum for each of the reference scenes; (e) calculating a k dimension eigen system for the ensemble average spectra and extracting N eigenvectors; (t) using the N eigenvectors for defining an N-dimension vector for each of the reference scenes; and (g) using the N-dimension vectors for preparing the reference template for the remote scenes classification; (b) using a second spectral imager for measuring a spectral cube of the remote scenes, such that a spectrum of each pixel in the remote scenes is obtained; (c) projecting the spectrum of each of the pixels into the N eigenvectors for obtaining a projected N dimension vector for each of the pixels; and (d) correlating each of the projected N dimension vectors with the reference template. Preferably, the method further includes the step of performing a spatial averaging procedure on all spectral slices.

Fifth, provided is a method of calculating decorrelation matched filters for remote scenes classification, the decorrelation matched filters being for extracting decorrelated spectral data from the remote scenes, the method comprising the step of (a) obtaining decorrelated spectral data characterizing a set of reference scenes via (i) classifying the set of reference scenes via a conventional classification technique for obtaining a set of preclassilied reference scenes; (ii) using a first spectral imager for measuring a spectral cube of the preclassified reference scenes; and (iii) employing a decorrelation statistical method for extracting the spectral cube for decorrelated spectral data characterizing the reference scenes; and (b) mathematically manipulating at least a part of the decorrelated spectral data for obtaining a mathematical description of the decorrelation matched filters.

According to a preferred embodiment of the invention the decorrelated spectral data is obtained using a principal component analysis, which includes expressing each of the reference scenes by a linear combination of N eigenvectors.

Sixth, provided is a set of decorrelation matched filters for remote scenes classification, the decorrelation matched filters being for extracting decorrelated spectral data from the remote scenes, the set includes physical filters having shapes, the shapes following a mathematical description, the mathematical description being obtainable by (a) obtaining decorrelated spectral data characterizing a set of reference scenes via (i) classifying the set of reference scenes via a conventional classification technique for obtaining a set of preclassified reference scenes; (ii) using a first spectral imager for measuring a spectral cube of the preclassified reference scenes; and (iii) employing a decorrelation statistical method for extracting the spectral cube for decorrelated spectral data characterizing the reference scenes; and (b) mathematically manipulating at least a part of the decorrelated spectral data for obtaining the mathematical description of the decorrelation matched filters.

Seventh, provided is a method of tuning a tunable filter for remote scenes classification, the method renders the tunable filter to mimic a set of decorrelation matched filters, and is for extracting decorrelated spectral data from the remote scenes, the method includes the steps of (a) obtaining decorrelated spectral data characterizing a set of reference scenes via (i) classifying the set of reference scenes via a conventional classification technique lbr obtaining a set of preclassified reference scenes; (ii) using a first spectral imager for measuring a spectral cube of the preclassified reference scenes; and (iii) employing a decorrelation statistical method for extracting the spectral cube for decorrelated spectral data characterizing the reference scenes; (b) mathematically manipulating at least a part of the decorrelated spectral data for obtaining a mathematical description describing the set of decorrelation matched filters; and (c) sequentially tuning the tunable filter according to the mathematical description.

In a preferred embodiment of the invention the tunable filter is selected from the group consisting of AOTF and LCTF.

Eighth, provided is yet another method for remote scenes classification. The method includes the steps of (a) preparing a reference template for classification of the remote scenes via (i) classifying a set of reference scenes via a conventional classification technique for obtaining a set of preclassified reference scenes; (ii) using a first spectral imager for measuring a spectral cube of the preclassified reference scenes; (iii) employing a decorrelation statistical method for extracting the spectral cube for decorrelated spectral data characterizing the reference scenes; and (iv) using at least a part of the decorrelated spectral data for the preparation of the reference template for the remote scenes classification; (b) calculating a mathematical description of decorrelation matched filters for classification of the remote scenes employing the reference template, the calculation being by mathematically manipulating at least a part of the decorrelated spectral data; (c) using the mathematical description of the decorrelation matched filters for manufacturing the decorrelation matched filters; (d) using the decorrelation matched filters for extracting decorrelated spectral data from each pixel of the remote scenes; and (e) comparing the decorrelated spectral data extracted from each pixel of the remote scenes with the reference template. Preferably, the method further includes the step of (f) attributing each pixel an artificial color according to the comparison.

Ninth, further according to the present invention provided is yet another method for remote scenes classification. The method includes the steps of (a) providing a set of decorrelation matched filters for the remote scenes classification, the decorrelation matched filters being for extracting decorrelated spectral data from the remote scenes, the set including physical filters having shapes, the shapes following a mathematical description, the mathematical description being achieved by (i) preparing a reference template for classification of remote scenes via (a) classifying a set of reference scenes via a conventional classification technique for obtaining a set of preclassified reference scenes; (b) using a first spectral imager for measuring a spectral cube of the preclassified reference scenes; (c) employing a decorrelation statistical method for extracting the spectral cube for decorrelated spectral data characterizing the reference scenes; and (d) using at least a part of the decorrelated spectral data for the preparation of the reference template for the remote scenes classification; and (ii) mathematically manipulating at least a part of the decorrelated spectral data for obtaining the mathematical description of the decorrelation matched filters; (b) using the decorrelation matched filters for extracting decorrelated spectral data from each pixel olfthe remote scenes; and (c) comparing the decorrelated spectral data extracted from each pixel of the remote scenes with the reference template. Preferably the method further includes the step of (d) according to the comparison, attributing each pixel an artificial color.

Tenth, further according to the invention provided is still another method for remote scenes classification. The method includes the steps of (a) providing a tunable filter and tuning information for tuning the tunable filter so as to mimic a set of decorrelation matched filters, the tunable filter being for extracting decorrelated spectral data from the remote scenes, the tuning information being achieved by (i) preparing a reference template for classification of remote scenes via (a) classifying a set of reference scenes via a conventional classification technique for obtaining a set of preclassified reference scenes; (b) using a first spectral imager for measuring a spectral cube of the preclassified reference scenes; (c) employing a decorrelation statistical method for extracting the spectral cube for decorrelated spectral data characterizing the reference scenes; and (d) using at least a part of the decorrelated spectral data for the preparation of the reference template for the remote scenes classification; (ii) mathematically manipulating at least a part of the decorrelated spectral data for obtaining the tuning information, which is a mathematical description describing the set of decorrelation matched filters; and (b) using the information for sequentially tuning the tunable filter for extracting decorrelated spectral data from each pixel of the remote scenes; and (c) comparing the decorrelated spectral data extracted from each pixel of the remote scenes with the reference template.

Eleventh, still according to the invention provided is a spectral decorrelation measurement apparatus for remote scenes classification by extracting decorrelated spectral data from the remote scenes, the apparatus is connected to a telescope used to view the remote scenes, the apparatus includes (a) a detector; and (b) an optical system for transmitting electromagnetic radiation from the remote scenes onto the detector, the optical system including a set of decorrelating matched filters, the decorrelation matched filters being for extracting decorrelated spectral data from the remote scenes, the filters of the set of decorrelation matched filters having shapes, the shapes following a mathematical description, the mathematical description being calculated by (i) obtaining decorrelated spectral data characterizing a set of reference scenes via (a) classifying the set of reference scenes via a conventional classification technique for obtaining a set of preclassified reference scenes; (b) using a first spectral imager tor measuring a spectral cube of the preclassified reference scenes; and (c) employing a decorrelation statistical method for extracting the spectral cube for decorrelated spectral data characterizing the reference scenes, and (ii) mathematically manipulating at least a part of the decorrelated spectral data for obtaining the mathematical description of the decorrelation matched filters. Preferably, the optical system further includes a collimating lens for collimating radiation reaching any of the decorrelating matched filters and focusing optics to image the scene on an array detector. Still preferably, the decorrelation matched filters are arranged on a rotatable filter carrying element.

Twelfth, provided is another spectral decorrelation measurement apparatus for remote scenes classification by extracting decorrelated spectral data from the remote scenes, the apparatus is connected to a telescope used to view the remote scenes, the apparatus includes (a) a detector; and (b) an optical system for transmitting electromagnetic radiation from the remote scenes onto the detector, the optical system including a tunable filter and a tuning device, the tuning device being for tuning the tunable filter, so that the tunable filter sequentially mimics a set of decorrelating matched filters, the decorrelation matched filters mimicked by the tunable filter being for extracting decorrelated spectral data from the remote scenes, the tuning of the tunable filter being calculated according to a mathematical description, the mathematical description being calculated by (i) obtaining decorrelated spectral data characterizing a set of reference scenes via (a) classifying the set of reference scenes via a conventional classification technique for obtaining a set of preclassified reference scenes; (b) using a first spectral imager for measuring a spectral cube of the preclassified reference scenes; and (c) employing a decorrelation statistical method for extracting the spectral cube for the spectral cube for decorrelated spectral data characterizing the reference scenes; and (ii) mathematically manipulating at least a part of the decorrelated spectral data for obtaining the mathematical description of the mimicked decorrelation matched filters.

Reference is now made to the following examples which demonstrate the principles of the method and the construction and operation of the hardware of the present invention.

The following examples focus on the analysis of human chromosomes. As opposed to remote scenes which are both large and remote and therefore are viewed via a telescope, chromosome samples are very small and close scenes viewed via a microscope. However, as will become apparent to the reader, in both cases the principles of the analysis are identical, since once a spectra cube is measured, the decorrelation statistical analysis that follows is substantially identical. Furthermore, spectral imagers which suit both remote as well as close scenes measurements are well known. One example is the SPECTRACUBE™ system described hereinabove which may be connected to various optical instruments including microscopes and telescopes. The nature of radiation obtained from the scene, be it reflected, emitted, or luminesced, be it in any spectral range, is also of no relevance to the type of analysis herein described. Once spectra of all the pixel of the scenes of a field of view are determined, the decorrelation analysis which follows is substantially the same. Thus, the following examples, together with the above descriptions, illustrate the invention.

EXAMPLE 1

Chromosome Preparationfor Measurement

The emergence of multicolor FISH has broadened the applications of molecular cytogenetics in basic research and genetic diagnosis. All existing multicolor FISH techniques require the use of fluorescent probes whose emission spectra can be separated with optical filters [Ried et al., (1992) Simultaneous visualization of seven different DNA probes by in situ hybridization using combinatorial fluorescence and digital imaging microscopy. Proc. Natl. Acad. Sci. USA 89, 1388–1392; and, Ried (January 1994) Fluoreszenz in situ Hybridizierung in der genetischen Diagnostik, Faculty of theoretical medicine, Ruprecht-Karls University Heidelberg, both are incorporated by reference as if fully set forth herein]. This requirement limits the number of dyes which can be distinguished in a given sample.

A novel approach for FISH, employing the SPECTRACUBE™ system to measure and analyze multiple spectrally overlapping labeled probes (single and combinatorial), to classify chromosomes and therefore to detect chromosomal aberrations was recently introduced in E. Schroeck et al. (1996) Multicolor spectral karyotyping of human chromosomes. Science, 273, 494–497, which is incorporated by reference as if fully set forth herein.

According to that novel approach, spectral bio-imaging which is a combination of Fourier spectroscopy, CCD-imaging and optical microscopy enabling the measurement of accurate spectral data simultaneously at all points of a biological sample, was used to visualize hybridization based multicolor appearance of all (i.e., 24) types of human chromosomes and to generate a color map of the human karyotype.

In the following examples, data spectrally collected by any spectral imager having a spectral resolution of 14 nm or higher (i.e., Δλ<14 nm) is statistically analyzed using decorrelation statistical methods, such as, but not limited to, principal component analysis (PCA) to find correlations among the data and to construct (i) a reference template which may then be used for routine analysis of new samples; and (ii) a hardware based on decorrelation matched filters (fixed or tunable) for collecting only the decorrelated spectral data (a smaller amount than with prior art), from new samples while the correlated data are averaged over at the outset, thereby decreasing measurement time and increasing signal to noise ratio. Both the reference template and the decorrelation matched filters (or their tuned mimics effected by a tunable filter) can be used to classify chromosomes and to detect chromosomal aberrations. Similarly, they can be used to analyze remote scenes.

As far as chromosomes are concerned, and as is described in greater detail below, both the reference template and the decorrelation matched filters (or their tuned mimics using a tunable filter) are dedicated to a given experimental procedure in which the dyes and their combinations which are used to label any of the chromosomes are predetermined.

It will be appreciated by one ordinarily skilled in the art that many different sets of fluorophores and combinations thereof can be used to specifically label each of the 24 chromosomes of human or each chromosome of any other species. In this example a set of five dyes from which combinations of up to three dyes are used to differently label each of the 24 human chromosomes is used.

Following is a description of the dyes and their combinations which are presently preferred, to which dyes and combinations the construction of a reference template and decorrelation matched filters as described in the Examples to follow are dedicated.

Thus, 24 chromosome paints (1 through 22, X and Y, Table 2), each labeled with a different combination of three or less different flourophores selected from a set of five fluorophores according to the combinatorial hybridization approach (a through e, Table 2), (see Table 2 for the different fluorophores and their spectral characteristics and Table 3 for the assignment of the iluorophores listed in Table 2 to obtain the 24 chromosome paints), were simultaneously hybridized with human mitotic chromosome spreads of few non-related male white blood cells, prepared for hybridization essentially as described in Ried et al. [Ried et al., (1992) Simultaneous visualization of seven different DNA probes by in situ hybridization using combinatorial fluorescence and digital imaging microscopy. Proc. Natl. Acad. Sci. USA 89, 1388–1392].

Hybridized chromosomes were viewed through an inverted fluorescence microscope connected to the SPECTRACUBE™ System and were analyzed.

TABLE 2

| Fluorophore | Symbol | Excitation (nm) |
|---|---|---|
| FITC or Spectrum Green | a | 475–495 |
| Cy5 ™[1] | b | 630–670 |
| Cy3 ™[1] | c | 540–570 |

TABLE 2-continued

| Fluorophore | Symbol | Excitation (nm) |
|---|---|---|
| Texas-Red | d | 540–570 |
| Cy5.5 ™[1] | e | 630–670 |

[1] from Amersham

TABLE 3

| Chromosome | Chromosome paint | Fluorophores |
|---|---|---|
| human chromosome 1 | 1 | b, c, d |
| human chromosome 2 | 2 | e |
| human chromosome 3 | 3 | a, c, e |
| human chromosome 4 | 4 | c, d |
| human chromosome 5 | 5 | a, b, e |
| human chromosome 6 | 6 | b, d, e |
| human chromosome 7 | 7 | b, c |
| human chromosome 8 | 8 | a, b, c |
| human chromosome 9 | 9 | a, d, e |
| human chromosome 10 | 10 | c, e |
| human chromosome 11 | 11 | a, c, d |
| human chromosome 12 | 12 | b, e |
| human chromosome 13 | 13 | a, d |
| human chromosome 14 | 14 | b |
| human chromosome 15 | 15 | a, e |
| human chromosome 16 | 16 | b, d |
| human chromosome 17 | 17 | a, c |
| human chromosome 18 | 18 | a, b, d |
| human chromosome 19 | 19 | c |
| human chromosome 20 | 20 | a |
| human chromosome 21 | 21 | d, e |
| human chromosome 22 | 22 | b, c, e |
| human chromosome X | X | c, d, e |
| human chromosome Y | Y | d |

EXAMPLE 2

Decorrelation Statistical Analysis for Chromosome Classification and for Designing Decorrelation Matched Filters.

Decorrelation statistical analysis is directed at extracting decorrelated data out of a greater amount of data, and average over the correlated portions thereof. There are a number of related statistical decorrelation methods. Examples include but not limited to principal component analysis (PCA), canonical variable analysis and singular value decomposition, etc., of these methods PCA is perhaps the more common one, and its use for decorrelation of spectral data, as this term is defined above, is hereinafter described.

However, considering the fact that all decorrelation statistical methods including those listed above are related to one another, there is no intention to limit the scope of the invention to use of any specific decorrelation statistical method.

Specifically, there is no intention to limit the scope of the present invention to use of principal component analysis, as any other decorrelation statistical method may be alternatively employed. Information concerning the use and operation of the above listed decorrelation statistical methods is found in R. A. Johnson and D. W. Wichen, "Applied Multivariance Statistical Analysis, third edition, Prentice Hall (1992) and T. W. Anderson, An Introduction to Multivariance Statistical Analysis, second edition , Wiley and Sons (1984), both are incorporated by reference as if fully set forth herein.

Furthermore, as will become apparent from the descriptions to follow, the implementation of a decorrelation statistical method may be done using various modifications. As the concept of the present invention is not dependent upon any specific modification, it is the intention that the scope of the present invention will not be limited to any specific modification as described below.

Principal component analysis (PCA) is one of a number of powerful techniques used in multivariate statistical analysis. It is advantageous in cases where a large number of "results", which depend on a large number of possibly correlated variables forms the basic data set. Its strength lies in the fact that this data decomposition provides a transformation to decorrelated variables, while simultaneously averaging over correlated variables.

In this paragraph the PCA technique as applied to multi-spectral images of the same field of view is delineated. The basic data set. i.e., the spectral cube, is composed of k spectral slices of the same field, where each spectral slice is obtained at a different spectral band. Thus, the data set is composed of the spectra of all the pixels of the field. One of the objectives of looking at such a data set can be the characterization of the pixels into groups of similar spectra. Regard each spectral slice as a vector whose elements are the image pixels arranged into the column vector using a predetermined code. Call the spectral slices $X_m$, so that the term $x_{nm}$ signifies the n-th pixel of the m-th spectral slice. In such way, the matrix $x=\{x_{nm}\}$ carries the full information, so that each column is a spectral slice. Define a matrix y derived from matrix x by subtracting from each column, the column average. The various columns of the y matrix may be correlated, so that, some of the information carried by the data is correlated. The PCA technique decorrelates the information and reduces it only to decorrelated variables, so that the amount of "real" data pixels is smaller and easier to handle.

The correlations are obtained directly by computing the covariance matrix c defined by Equation 2:

$$c = y'y \quad (2)$$

where y' is the transpose of y. The i,j term of C is the covariance of the i-th slice with the j-th slice, i.e. if they are decorrelated this term vanishes. The diagonal of c is composed of the variances of each spectral slice, which can be regarded as a scale for the amount of information in this particular slice. Alternatively, this variance (its square root) can be regarded as the average contrast of this particular slice.

Linear algebra describes this situation as follows. The elements of interest (i.e., the pixels of the spectral slices, k of them) are points in a k dimensional space. The fact that the covariance matrix c shows correlations is represented by its having a rank smaller than k. This situation is called degeneracy and it means that the k (narrow band) spectral slices provide too much data relative to the information content. Reduction of the data is performed by finding the eigen system of the covariance matrix. Formally, this operation means that one has to find k vectors $v_m$ called eigenvectors and k scalars $\lambda_m$ called eigenvalues so that (Equation 3):

$$c \cdot v_m = \lambda_m v_m \quad (3)$$

for m=1, 2, . . . , k

In a case where the data is correlated, some of the eigenvalues vanish. The number of non-vanishing eigenvalues defines the dimension of the information, which dimension is smaller than k. The corresponding eigenvectors define a subspace in the original k space in which the full information content is represented. Furthermore, the information in each new dimension is completely decorrelated to the information in the other dimensions. Thus in the new space the full information content is represented in a decorrelated manner so that it can be easily used for classification purposes.

For remote sensing one would preferably add an additional step of segmentation of the interesting scenes to be analyzed, for the construction of the eigenvectors of the covariance matrix, to obtain a result which is not affected by the varying background or clutter present between the interesting scenes. This step is performed just before the construction of the covariance matrix, so that this matrix contains only information on the scenes to be analyzed and not of the uninteresting scenes, which are regarded as background.

For further details regarding the principal component analysis, the reader is referred to Martens and Naes (1989) Multivariate Calibration, John Wiley & Sons, Great Britain; and to Esbensen et al., Eds. (1994) Multi variance analysis—in practice, and, Computer-aided modeling as CAMO, and the Unscrambler's User's guide Trondheim, Norway, both are incorporated by reference as if fully set forth herein.

It should be noted that such an analysis can be performed on a whole spectral cube. Preferably, the analysis is performed only for selected pixels or mathematically manipulated (e.g., after background or interferences subtraction and averaging) selected pixels to improve the results and enable better classification later on. The preferred approach is described in more detail below, nevertheless, there is no intention to limit the scope of the present invention to the preferred approach employed, as different mathematical manipulations may be found useful for different data collection approaches (e.g., filter or dispersion element based spectral imagers) and/or different radiation employed.

EXAMPLE 3

The Basic Data Set

The results of the spectral measurements of the stained chromosomes sample are stored in a spectral cube in any convenient format. In order to be able to access, for analysis purposes, each spectral cube, a conversion is typically needed. The conversion can be performed by a dedicated software able to read each pixel in each spectral slice and write it into another file in a format suitable to the user. Alternatively, a commercial software, sold under the name ENVI (environment for visualizing images) by Research Systems Inc., Boulder Colo., USA, can be used. ENVI can read a spectral cube and write, on request, each spectral slice into a standard *.GIF format which can be read by a large number of routines. ENVI can be used in a different mode called the BSQ format. The later writes the cube in a binary sequential manner, starting at the spectral slice possessing the highest wave number, wherein each slice is written column after column.

All this can be done also with Matlab, a popular mathematical analysis software and programming environment, with the addition of special software packages able to read the spectral cubes.

Alternatively to the above approach, a dedicated software package can be written in an appropriate language, either stand alone or incorporated in the existing SPECTRACUBE™ system software, to perform the building of the basic data set.

Both the GIF and the BSQ methods convert the data in an exact fashion, yet there is a difference that a user should be aware of. While converting by using the GIF transformation, each spectral slice is stretched to the full dynamic range thus loosing the relative intensities among the various spectral slices, but conserving the full information content in each, whereas according to the BSQ conversion, the entire spectral cube is converted, preserving the relative intensities in the entire cube. In a case where the user wishes to further perform a stretch, the user can do it afterwards. This difference affects the PCA in a marginal way. Presently, the GIF approach is preferred.

For the present analysis twenty spectral slices derived from a spectral cube measured as described above were used. These were chosen out of a larger number of spectral slices of the cube. The spectral slices utilized were those where significant contrast and low noise was present. It should be noted that any other number of spectral slices from about 10–15 or more (up to a limit which is determined by the spectral resolution of the spectral imager and the spectral range) can be used and that there is no intention to limit the scope of the invention to any specific number.

Figure 3A:
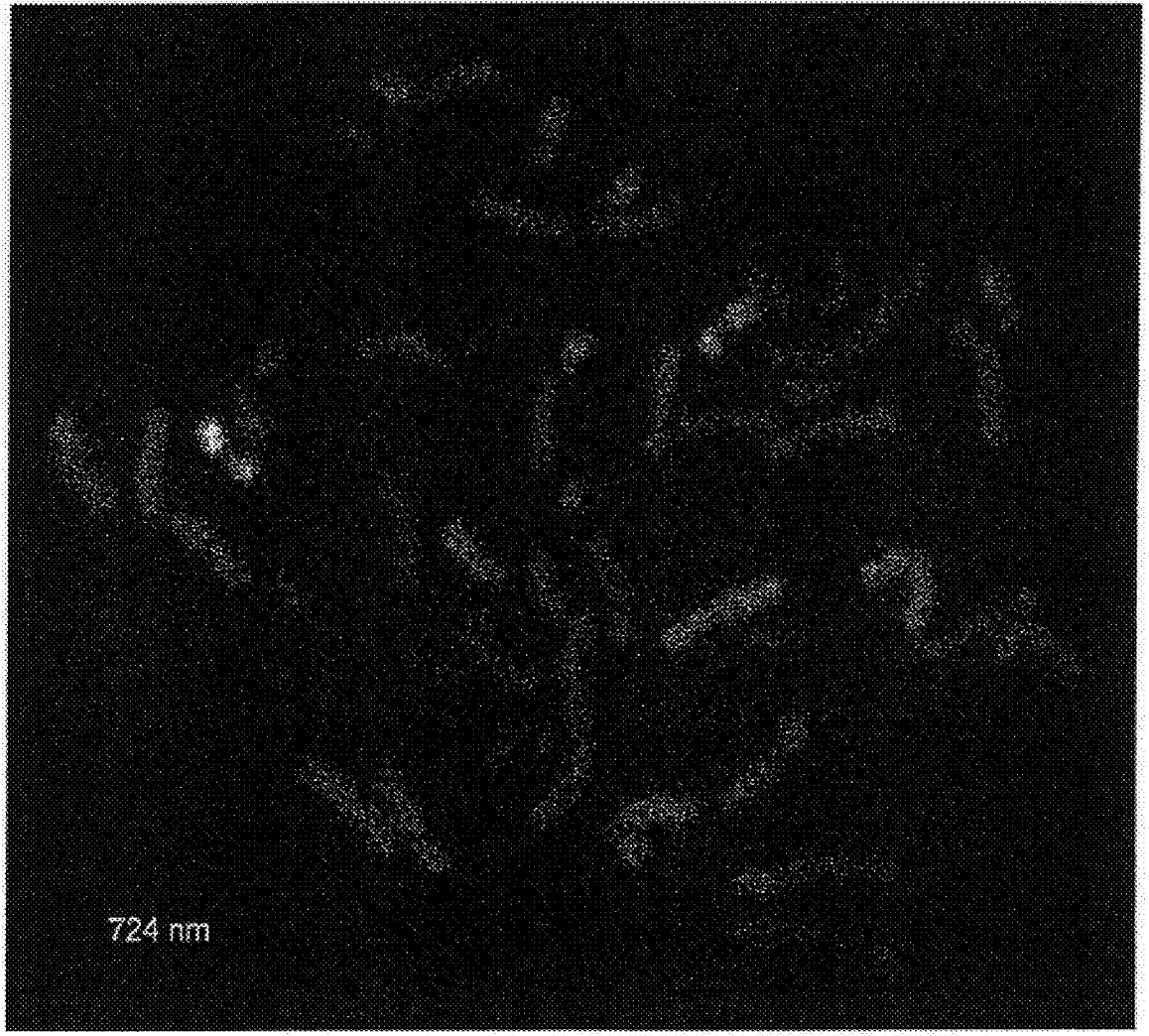
FIGS. 3a and 3b are chromosome images at spectral bands 724 nm and 597 nm, respectively, as derived from a spectral cube measured using the SPECTRACUBE™ system.
Figure 3B:
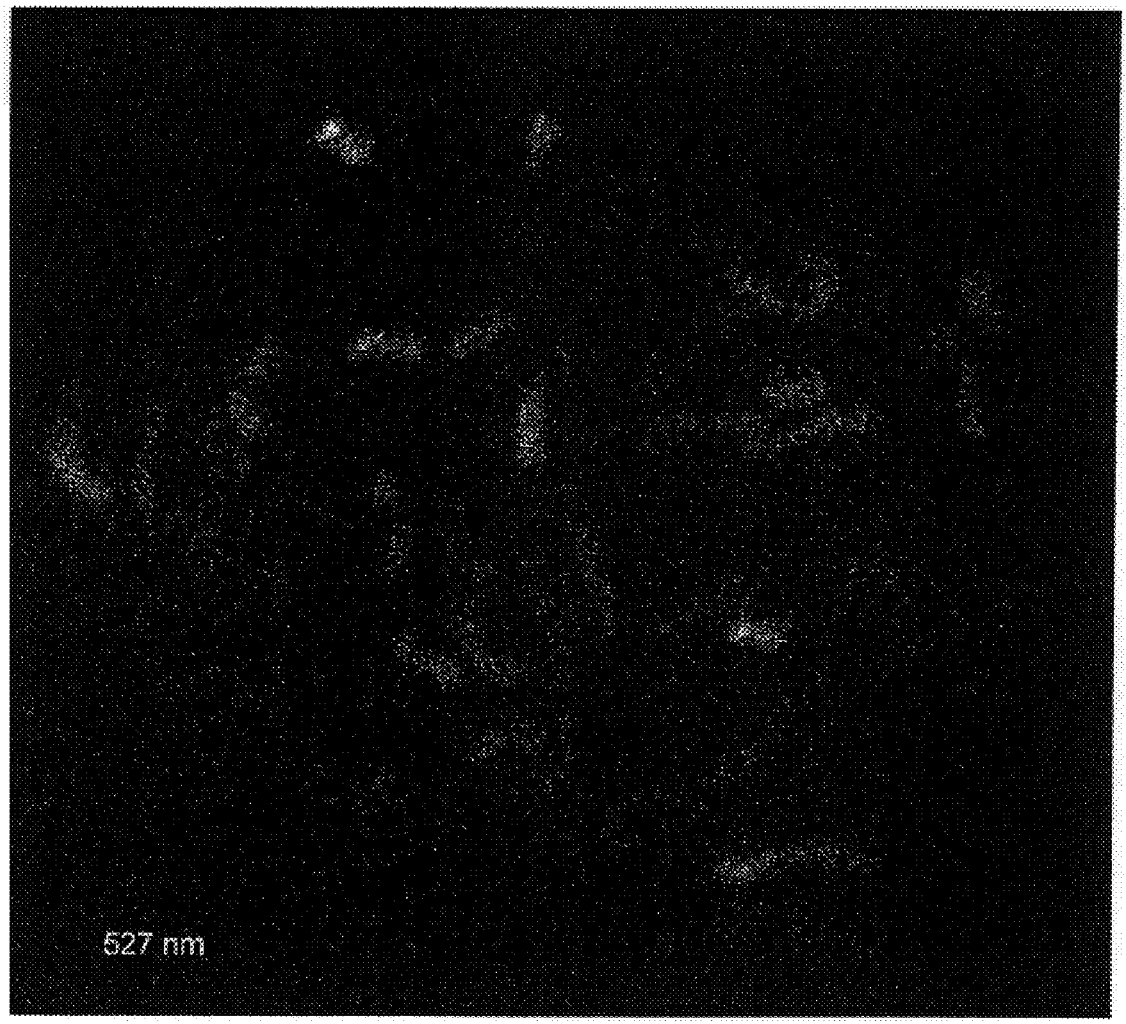

FIGS. 3a–b, present two examples of the spectral slices, at 724 nm (FIG. 3a) and 597 nm (FIG. 3b). Notice the difference in contrast, noise and intensity over the various chromosomes.

EXAMPLE 4

Pre-Processing for Classification

For pre-processing, the k (e.g., twenty) spectral slices above are first used to find the decorrelated (and therefore orthogonal) principal components vectors of each chromosome type (L types in a species, 24 types in human), then the projection of each chromosome in each relevant principal component direction is calculated. This is equivalent to find the position of each chromosome template in the principal component space. This is performed by first identifying the chromosomes via conventional chromosome classification techniques, e.g., G-banding, R-banding or color karyotyping as described in E. Schroeck et al. (1996) Multicolor spectral karyotyping of human chromosomes, Science, 273, 494–497. It should be noted that the method described in Science magazine can be performed post G-banding or simultaneously to R-banding without affecting the measured spectral results.

As each of the chromosomes is labeled with a different fluorophore or a different combination of fluorophores, the projection of each chromosome onto each of the orthogonal principal components (PCs) forms a specifying reference vector (24 different vectors for a human male, 23 for a human female, different numbers for other species, generally L vectors for a species) which is unique to each of the chromosomes.

These L reference vectors collectively form a reference template for chromosome classification, as each of these L reference vectors is used as an identification means to attribute each pixel of a new spectral cube to one of the L chromosome types.

Therefore, these L different reference vectors, i.e., the reference template, can now be used to form an artificially colored karyotype of any spectral cube in which each of the chromosomes is attributed a different artificial color according to its type, selected from the L types of chromosomes in the studied species. This is done by a classification algorithm which compares measured vectors of pixels in a cube to be analyzed to the above reference vectors, followed by attributing each of the pixels a matching artificial color selected from L different artificial colors, according to the comparison results.

A preferred embodiment for pre-processing for classification is herein described in more detail:

For each staining technique at least one, preferably a number, of independently classified (e.g., G-banding) images are selected, from which a reference template is calculated as follows.

First, a 3×3 spatial averaging is performed on all selected k spectral slices such that each nine pixels are now attributed an average spectrum and are considered a single enlarged pixel. Although this procedure reduces the spatial resolution of the analysis, it is employed as it also reduces noise to a large extent. It should however be noted that this step was experimentally determined to be useful, yet as the amount of noise associated with other data collection approaches and/or experimental procedures may differ tremendously, there is no intention to limit the invention to a specific mode of averaging (e.g., 3×3) or to averaging altogether.

Second, an average spectrum of the whole cube(s), or the average spectrum of some, most or all the background pixels is calculated and is thereafter subtracted from the spectrum of each of the pixels in the cube. It will be appreciated that as most of the pixels in a cube are of background, the different calculated average spectra yield nearly identical results. Nevertheless, it should be noted that as the intensity of background may differ to a large extent while using other data collection approaches and/or experimental procedures, different background subtraction procedures may be employed. Furthermore, as in some cases background subtraction may be found improving results in a marginal way only, it may therefore, in these cases, be discarded altogether.

Third, each chromosome is masked, typically manually or with a suitable automatic image processing algorithm, and the average spectrum for each chromosome within its mask is calculated. As mentioned above under Example 2, the analysis can be performed on a whole spectral cube(s), yet preferably, the analysis is performed only for selected pixels or mathematically manipulated (e.g., after background subtraction and averaging) selected pixels to improve the results and enable better classification later-on.

Fourth, the average spectrum of each chromosome calculated above is separately stretched preferably into the maximal dynamic range 0–1.

Fifth, the stretched average spectra of the same chromosome types derived from different or same cube measurements is averaged to produce an ensemble average spectrum for each type of chromosome (collectively L types, 24 types for human). As is now apparent, presently it is preferred that the PCA will be performed on mathematically manipulated pixels. These are L (e.g., 24 for human) pixels each having a unique ensemble average spectrum which are mathematically manipulated as described. It should be noted, however, that one can obtain similar results also when applying the above described steps in a different order.

Sixth, an eigen system of the ensemble average spectra is calculated and the eigenvectors are used to calculate the PC of the ensemble average spectra.

To this end, the L chromosomes ensemble average spectra are stored in an L (e.g., 24 for human) line by k (e.g., 20) columns matrix, called matrix S, where each line represents a chromosome and each column a given spectral slice which are selected as described above under Example 2. The number k of spectral slices is not necessarily 20 and can be any number between substantially 10–15 or more, say 40, about equally spaced in the 500–800 nm region, depending on the emission spectra of the fluorophores employed, k is preferably selected to be an integer greater than nine.

C is defined as the covariance of S. C is typically a k×k (e.g., 20×20) matrix which represents the covariance between each pair of chromosomes. The eigen system of matrix C is calculated. V is defined as the matrix composed of the eigenvectors (each column being an eigenvector).

Figure 4:
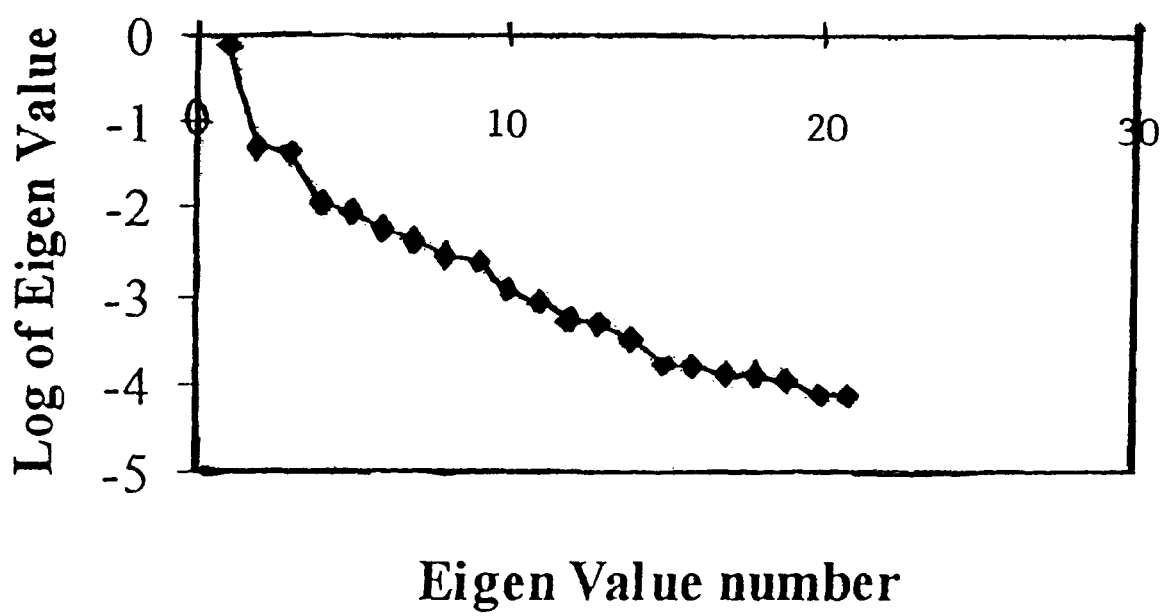
FIG. 4 is a graphic presentation of the twenty eigenvalues of the covariance matrix of the same spectral cube.
Figure 5A:
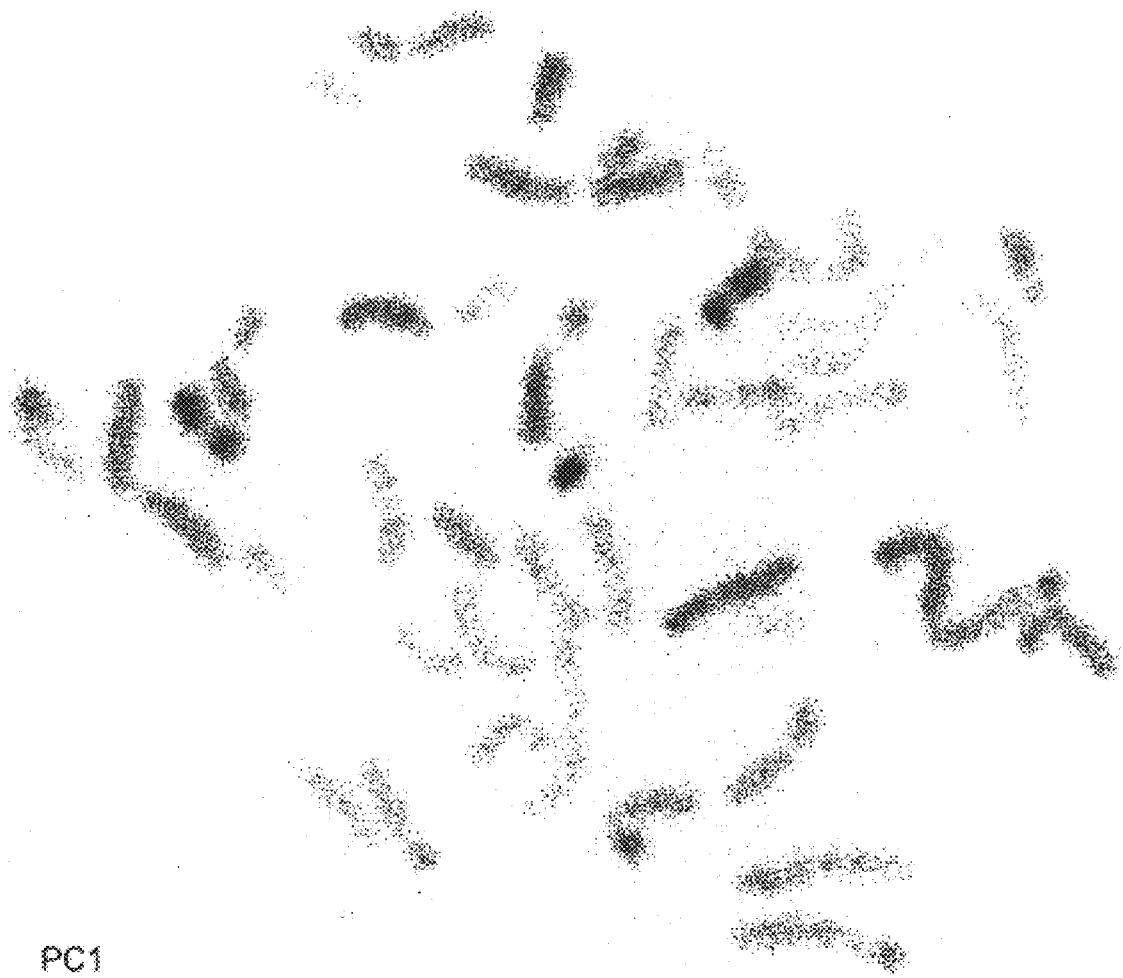
FIGS. 5a–e are the first five PCA images of the same spectral cube, shown after cube stretching to cover the full dynamic range of the display.
Figure 5B:
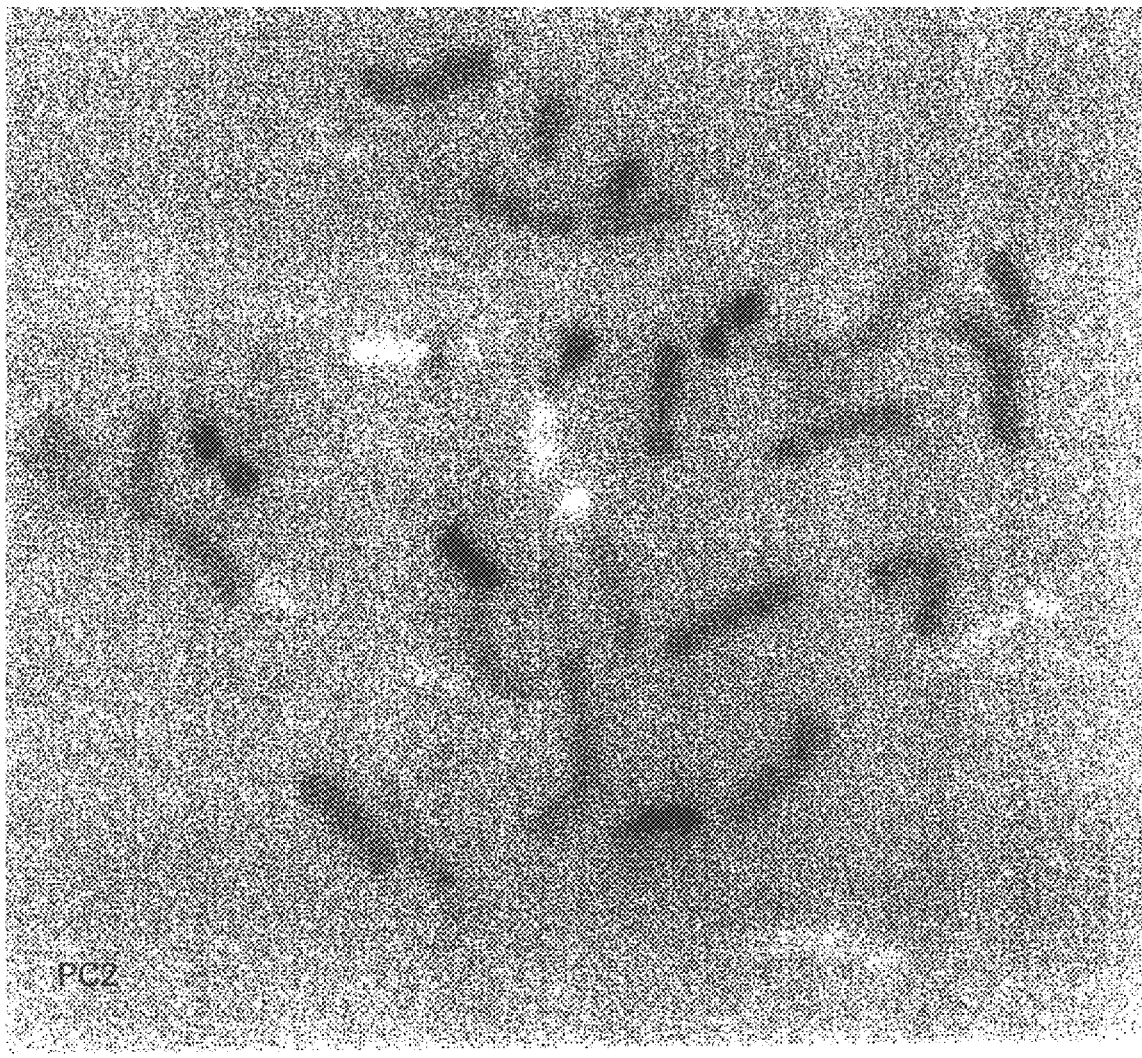
Figure 5C:
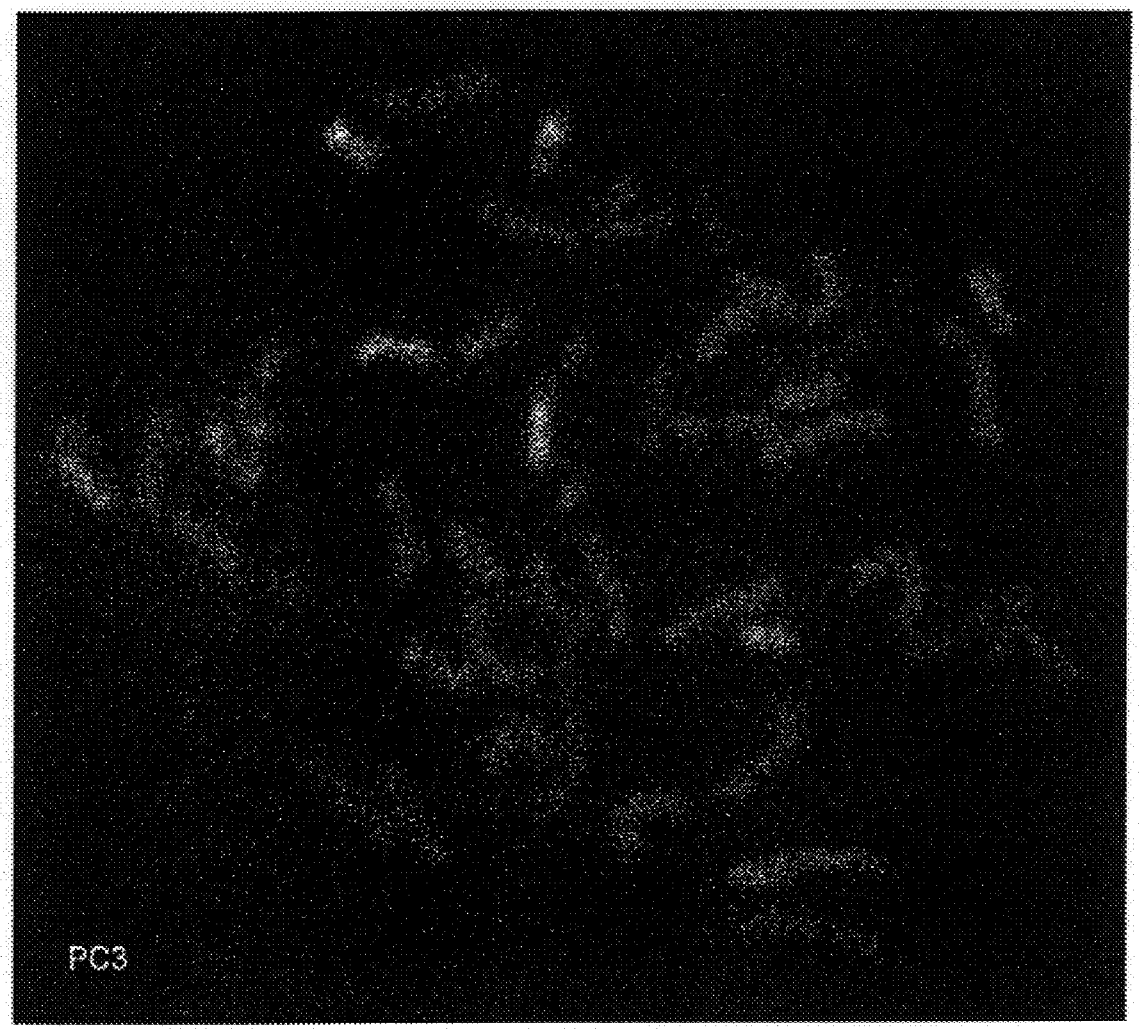
Figure 5D:
Figure 5E:
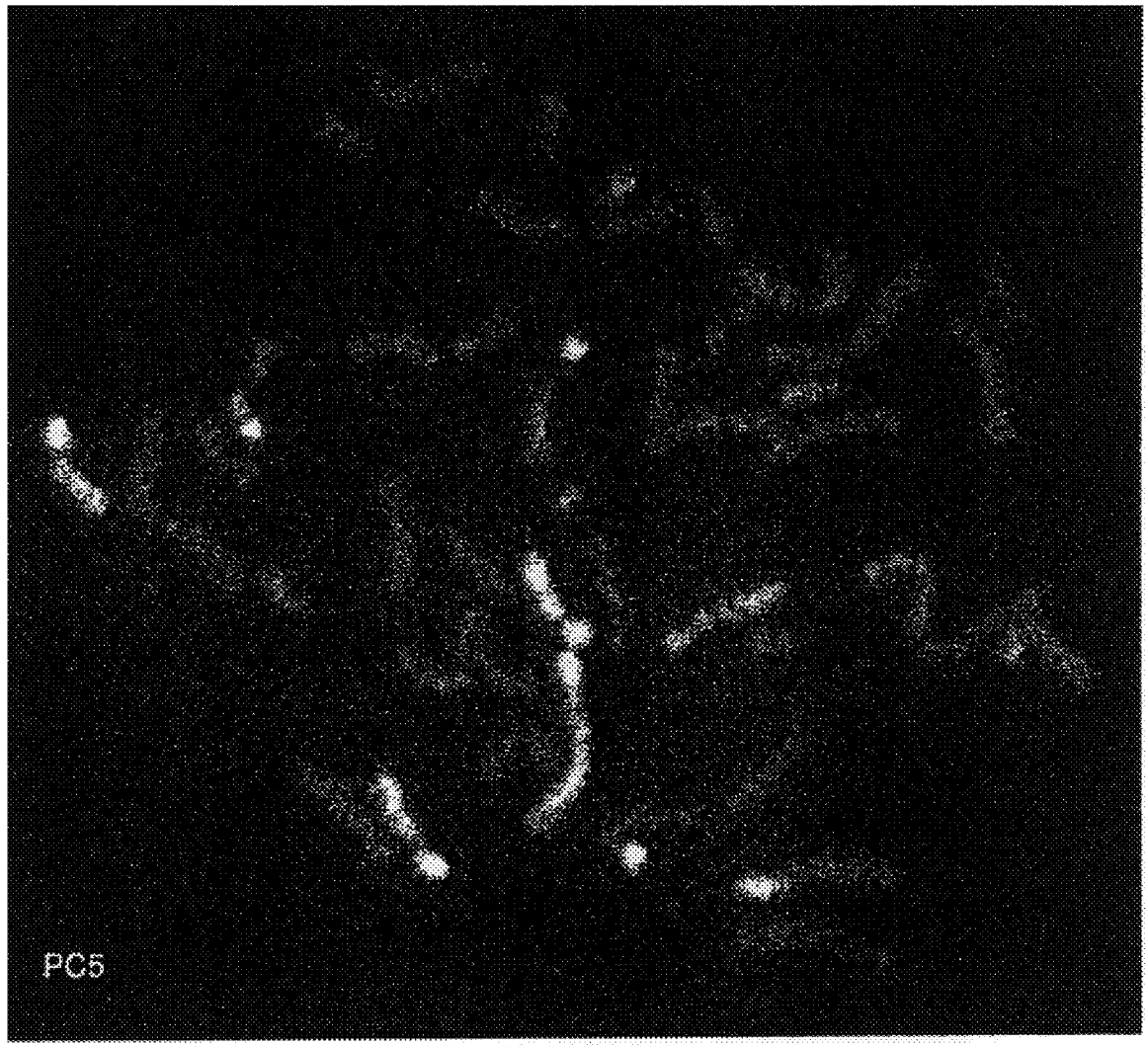

FIG. 4 presents 20 eigenvalues corresponding to these eigenvectors in decreasing order. Please note that this is a logarithmic display. From the graph presented in FIG. 4, one notices that the eigenvalues decrease very sharply with increasing number. From the point of view of the information content of the spectral cube, one can say that more than 95% of the information is contained in the first PCA image. On observing the PCA images, one notices that the chromosomes do appear only in the first 7 components, the first five of which are shown in FIGS. 5a–e.

Table 4 presents the first five (most significant) eigenvectors (Vec 1–Vec 5) for this system. Vec 1 being the most significant, whereas the first 20 lines of each column represent the relative weight of the wavelength depicted in the leftmost column. FIG. 6 is a graphic presentation of the first five vectors of matrix V.

TABLE 4

| 1 | Vec 1 | Vec 2 | Vec 3 | Vec 4 | Vec 5 |
|---|---|---|---|---|---|
| 522 nm | 0.012 | 0.023 | 0.251 | 0.011 | −0.010 |
| 526 nm | 0.016 | 0.030 | 0.328 | 0.003 | −0.007 |
| 530 nm | 0.018 | 0.035 | 0.388 | −0.003 | −0.003 |
| 534 nm | 0.019 | 0.040 | 0.430 | −0.006 | −0.002 |
| 543 nm | 0.018 | 0.047 | 0.454 | −0.018 | −0.008 |
| 548 nm | 0.014 | 0.045 | 0.411 | −0.035 | 0.000 |
| 552 nm | 0.009 | 0.037 | 0.323 | −0.052 | 0.013 |
| 593 nm | −0.046 | 0.050 | 0.003 | 0.191 | 0.579 |
| 599 nm | −0.151 | 0.108 | 0.013 | 0.194 | 0.615 |
| 610 nm | −0.470 | 0.261 | −0.002 | 0.058 | 0.205 |
| 616 nm | −0.562 | 0.303 | −0.016 | −0.017 | −0.121 |
| 629 nm | −0.399 | 0.201 | 0.001 | −0.092 | −0.286 |
| 635 nm | −0.228 | 0.119 | −0.013 | −0.092 | −0.220 |
| 670 nm | −0.103 | −0.198 | 0.022 | 0.283 | −0.071 |
| 678 nm | −0.204 | −0.383 | 0.055 | 0.435 | −0.095 |
| 693 nm | −0.304 | −0.553 | 0.089 | 0.271 | −0.096 |
| 710 nm | −0.222 | −0.400 | 0.042 | −0.385 | 0.134 |
| 727 nm | −0.143 | −0.262 | −0.001 | −0.548 | 0.185 |
| 745 nm | −0.096 | −0.183 | 0.012 | −0.297 | 0.154 |
| 765 nm | −0.052 | −0.089 | −0.001 | −0.148 | 0.021 |

The chromosome spectra in the decorrelated space, is calculated using Equation 4:

$$SS = S * V \quad (4)$$

wherein in the given example SS is a 24 by 20 matrix. It should be noted that, only N eigenvalues are of significance, typically 3–5, thus for chromosomes, typically N is selected to be an integer greater than two. Consequently only about N (e.g., 3 to 5) out of the k (e.g., 20) numbers composing a line of SS in the given example are of any significance, additional eigenvectors and eigenvalues are of marginal significance and may therefore be discarded. In the following, it is assumed that five (e.g., N=5) are significant, although a smaller number can be used.

Thus, a chromosome is uniquely specified by its N (e.g., 5) coordinates in the N-dimensional space with respect to the N chosen eigenvectors (and eigenvalues). These N coordinates represent the coefficients of the linear combination of the chromosome in question with respect to the N orthogonal eigenvectors. Using this type of analysis as compared with forming the matrix S for all the pixels in the cube (instead of only L mathematically manipulated pixels) ensures that (i) background pixels are not introduced into the calculation, and therefore the noise associated with them is avoided, and that (ii) each of the chromosomes is equally represented in terms of number of pixels. Table 5 presents an example of a truncated SS matrix. In this Table each row represents the projection of a given human chromosome on the five orthogonal eigenvectors or principal components (PCs) describing the spectral cube(s).

TABLE 5

| | PC No. 1 | PC No. 2 | PC No. 3 | PC No. 4 | PC No. 5 |
|---|---|---|---|---|---|
| Chr. 1 | −0.637 | −0.200 | 0.132 | −0.002 | 0.110 |
| Chr. 2 | −0.204 | −0.145 | 0.075 | −0.090 | 0.068 |
| Chr. 3 | −0.407 | −0.012 | 0.205 | −0.053 | 0.118 |
| Chr. 4 | −0.521 | 0.051 | 0.074 | −0.003 | 0.091 |
| Chr. 5 | −0.329 | −0.258 | 0.193 | −0.053 | 0.079 |
| Chr. 6 | −0.748 | −0.374 | 0.139 | −0.079 | 0.090 |
| Chr. 7 | −0.432 | −0.249 | 0.117 | −0.003 | 0.098 |
| Chr. 8 | −0.229 | −0.107 | 0.105 | 0.006 | 0.065 |
| Chr. 9 | −0.387 | −0.041 | 0.139 | −0.030 | 0.088 |
| Chr. 10 | −0.285 | −0.073 | 0.072 | −0.052 | 0.122 |
| Chr. 11 | −0.317 | 0.020 | 0.121 | −0.021 | 0.065 |
| Chr. 12 | −0.306 | −0.281 | 0.107 | −0.062 | 0.066 |
| Chr. 13 | −0.782 | 0.067 | 0.276 | 0.002 | 0.112 |
| Chr. 14 | −0.430 | −0.510 | 0.131 | −0.002 | 0.060 |
| Chr. 15 | −0.293 | −0.107 | 0.273 | −0.111 | 0.092 |
| Chr. 16 | −1.180 | −0.519 | 0.175 | 0.010 | 0.093 |
| Chr. 17 | −0.244 | 0.040 | 0.186 | 0.005 | 0.102 |
| Chr. 18 | −0.726 | −0.271 | 0.290 | −0.013 | 0.077 |
| Chr. 19 | −0.311 | 0.069 | 0.057 | 0.014 | 0.117 |
| Chr. 20 | −0.261 | 0.010 | 0.381 | −0.034 | 0.086 |
| Chr. 21 | −0.782 | −0.109 | 0.125 | −0.120 | 0.101 |
| Chr. 22 | −0.581 | −0.462 | 0.145 | −0.046 | 0.158 |
| Chr. X | −0.686 | −0.011 | 0.087 | −0.070 | 0.107 |
| Chr. Y | −1.681 | 0.206 | 0.117 | −0.049 | 0.068 |

Collectively, the vectors of Table 5 form a reference template which may therealter be used for classification of all the 24 chromosomes of a newly and similarly measured cube, as described hereinbelow in the following Examples.

Thus, for this example, given a measured spectrum (possibly background subtracted and averaged as described above) $M_i$, i=1–20, and a reference template of a set of eigenvectors $V_{ij}$, i=1–20 (wavelengths) j=1–5 (generally, i=1–k, whereas j=1–N), of which 1 is the most significant, then the five coordinates of $M_i$ in the five-dimensional space defined by the five PCs representing this spectrum are given by Equation 5:

$$P_k = \sum_{i=1}^{20} M_i V_{ik} \quad k = 1\text{–}5 \quad (5)$$

Each of these L (24 in the given example) N-dimension vectors (five-dimension vectors in the given example), P, is checked, by calculating the correlation, against the L template vectors, in order to decide to which chromosome type it belongs.

These L N-dimension vectors may then serve as attraction centers for classification as delineated hereinbelow.

It should be noted that when the term 'attraction center' is used herein it refers to a statistical method capable of attributing a pixel to a chromosome. Examples include but are not limited to (i) a minimum "distance" calculation in the N-dimensional space according to Equation 5, in which a "distance" is defined (for example the Euclidean definition or square root of the sum of the squares of the coordinate differences) and then the chromosome which is "closer" according to this definition is chosen, or (ii) a maximum correlation calculation in which the scalar products between the pixel vector and the L template vectors are calculated, and then the one that gives the highest result is chosen.

EXAMPLE 5

Classification

A preferred embodiment for classification of a new spectral cube of chromosomes is herein presented:

First, a 3×3 spatial averaging is performed, if required, as described above.

Second, the average spectrum of the whole cube, or the average spectrum of some, most or all the background pixels is calculated and is thereafter subtracted from the spectrum of each of the pixels in the cube, similar to as described above, if required.

Third, the spectrum of each pixel in the cube is projected onto the average spectra principal domain, which is, in the preferred embodiment the 10–15 or more, e.g., 40, preferably 20 dimension space of wavelengths or in other words the k spectral slices, to obtain an N dimension vector for each pixel. In a preferred embodiment, projection of the spectrum of each of the pixels is via the scalar product of the spectrum vector with the orthogonal base vectors of the PC space.

Finally, the correlation of each of the projected spectra with all of the L N-dimension vectors (24 5-dimension vectors in the given example), which serve as attraction centers as described under Example 4, is calculated, and the L N-dimension vectors which gives the highest correlation is chosen as the chromosome to which that pixel is attributed to.

For color presentation, pixels attributed to each of the L (24 in the given example) different chromosome types are given a different artificial color to yield an L (24) color karyotype.

Figure 7:
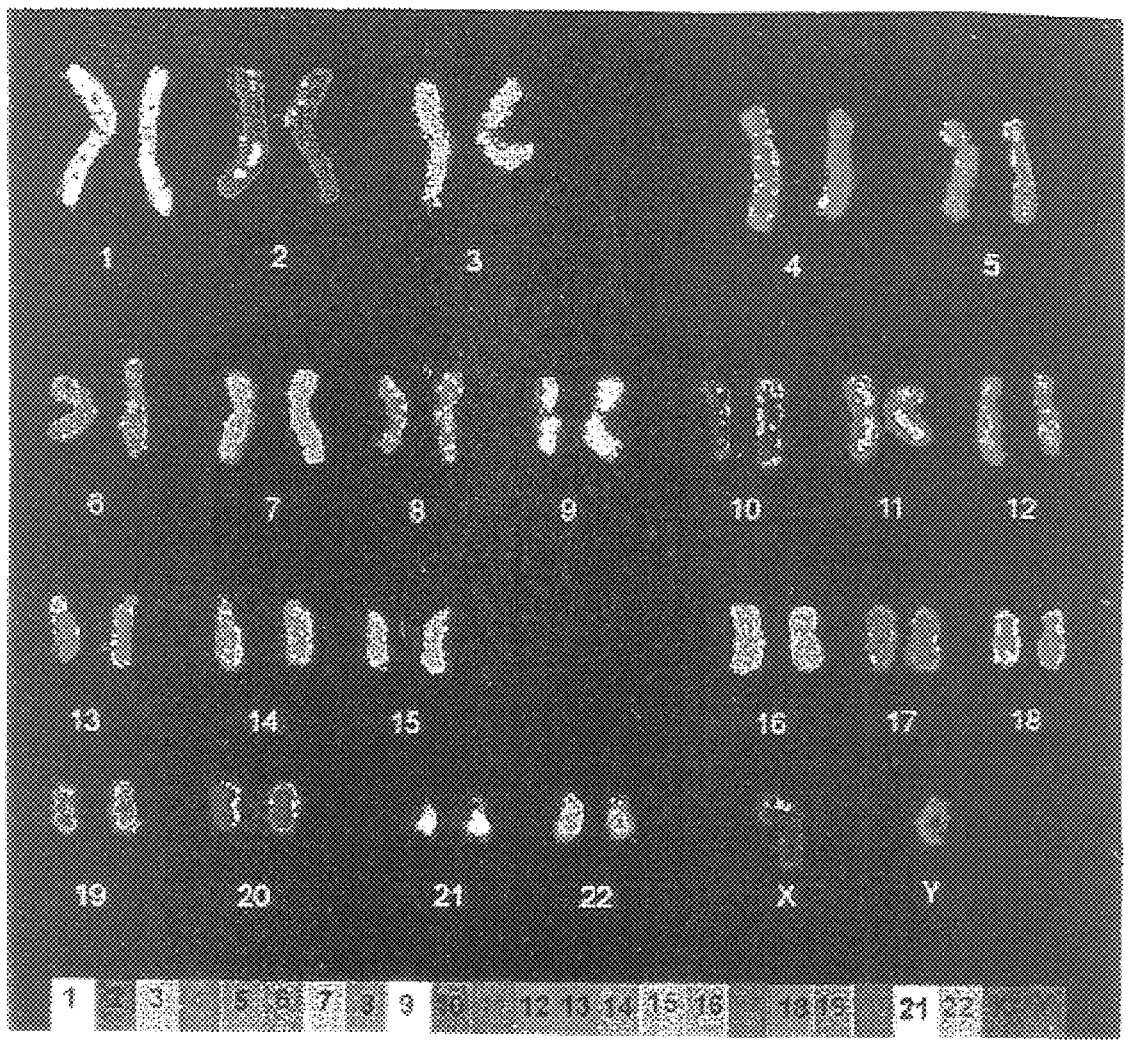
FIG. 7 is a male color karyotype obtained using the first five PCs, the karyotype is arranged in chromosome pairs.

FIG. 7 presents such a color karyotype, wherein the 24 chromosome types are arranged in pairs. Further presented in FIG. 7 is a color key, according to which the chromosomes can be identified.

Figure 8A:
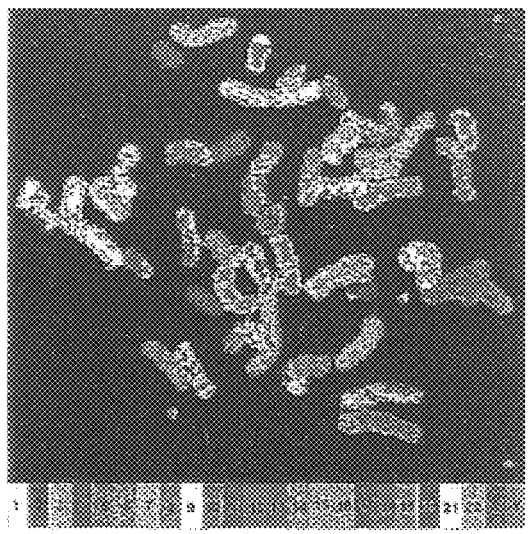
FIG. 8a–c are three male color karyotypes, prior to arrangement of the chromosomes in pairs, obtained using the first three, four and five PCs, respectively.
Figure 8B:
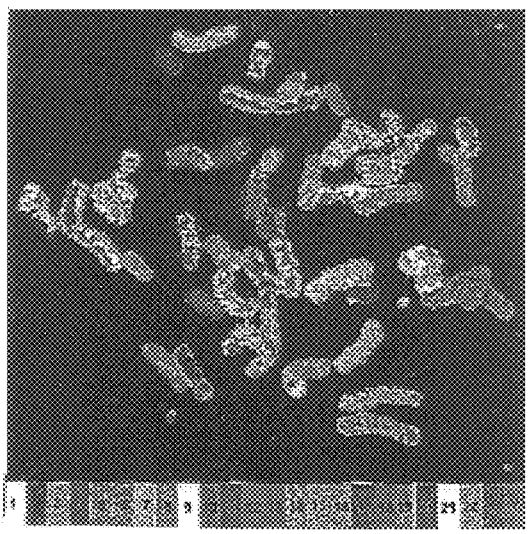
Figure 8C:
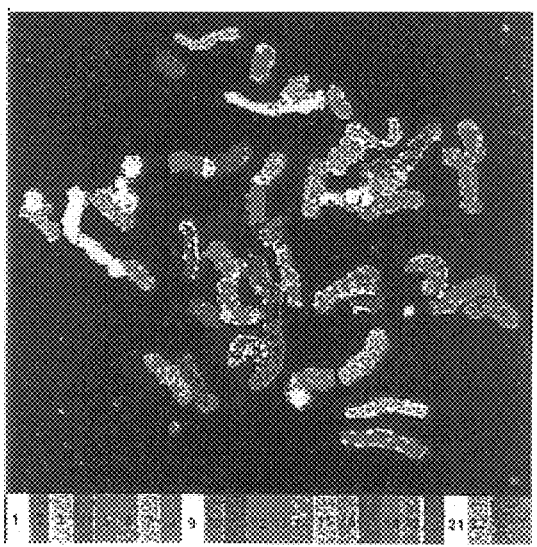

FIGS. 8a–c present color karyotyping results obtained using 24 N-dimension vectors, wherein N equals 3, 4 and 5, respectively. Please note that best results are achieved using 24 5-dimension vectors (FIG. 8c), yet, good results are obtained also with 24 4-dimension vectors (FIG. 8b). Furthermore, please note that using 24 3-dimension vectors as in FIG. 8a enables unambiguous color classification of most chromosome pairs. These results are not surprising considering the above mentioned fact that more than 95% of the information is contained in the first PCA image.

EXAMPLE 6

Decorrelation Matched Optical Filters

In the following paragraphs, described is the possibility of utilizing a small number of predetermined optical filters, referred herein as decorrelation matched filters or matched filters, in order to classify chromosomes using their fluorescent spectra, after a specific chromosome staining protocol is applied.

This new concept is based on the above described work using data from a spectral cube and a decorrelating statistical analysis such as principal component analysis, for data reduction.

After the chromosome staining technique is applied, each chromosome possesses a specific spectra. Thus chromosome classification is performed by matching the spectra to a predetermined template which is derived using for example PCA.

However, the nature of these specific spectra is such that there is a strong correlation among them all. Applying the PCA, which is one of the existing decorrelation techniques available, reveals that the chromosome specific spectra are linear combinations of a small number of "basis" spectra, the principal components or eigenvectors of the covariance matrix. The number of "basis" spectra being somewhere between 3 and 5. Consequently, the measurement and data analysis can be simplified by using specific hardware rather than imaging spectroscopy.

The construction of the specific hardware according to the present invention is as follows. Spectral imaging spectroscopy and decorrelating statistical analysis are utilized, as described above, to calculate the reference vectors and template.

The P N-dimension vectors, wherein N is an integer greater than two, e.g., three or five, for each pixel of the image, can be measured directly, using imaging microscopy and N pre-designed filters.

Observing Equation 5 above, defining the P vector, one realizes that it represents, mathematically at least, a filtration of the spectrum M. Physically it is not filtration as V has negative values as well. This problem however can be solved by a simple mathematical manipulation as follows:

Equation 6 defines a physical filter F (representing transmission in the range 0–1):

$$F_{ik} = \frac{V_{ik} - V_{ik\,min}}{V_{ik\,max} - V_{ik\,min}}, k = 1-N \qquad (6)$$

where $V_{ik\,min}$ equals minimum $(V_{ik})$ over all i, and $V_{ik\,max}$ equals maximum $(V_{ik})$ over all i.

There are of course N such filters (one for each k), wherein N is an integer greater than two, e.g., three or five. These N filters are physically realizable.

Using these filters, each pixel in the image can be measured to produce an N-dimension vector for each.

A pixel whose spectrum is $M_i$, i=1–20, will produce a PP N-dimension vector described by Equation 7:

$$PP_k = \sum_{i=1}^{20} M_i F_{ik}, k = 1-N \qquad (7)$$

One observes that the PP vectors and the P vectors are connected and the P vector can be calculated using Equation 8:

$$P_k = \Sigma M_i V_{ik} = (V_{ik\,max} - V_{ik\,min}) PP_k + V_{ik\,min} \Sigma M_i \qquad (8)$$

All the components of the V vectors are known from the stage of reference template preparation described hereinabove under Example 4. Table 6 represents the minimum and maximum value of the eigenvectors shown in Table 4 above. The sum $\Sigma M_i$ is the intensity of the pixel under discussion, which is measured directly from the microscope (no filter used).

TABLE 6

|     | Vec 1  | Vec 2  | Vec 3  | Vec 4  | Vec 5  |
| --- | ------ | ------ | ------ | ------ | ------ |
| min | −0.562 | −0.553 | −0.016 | −0.548 | −0.286 |
| max | 0.019  | 0.303  | 0.454  | 0.435  | 0.615  |

Figure 9:
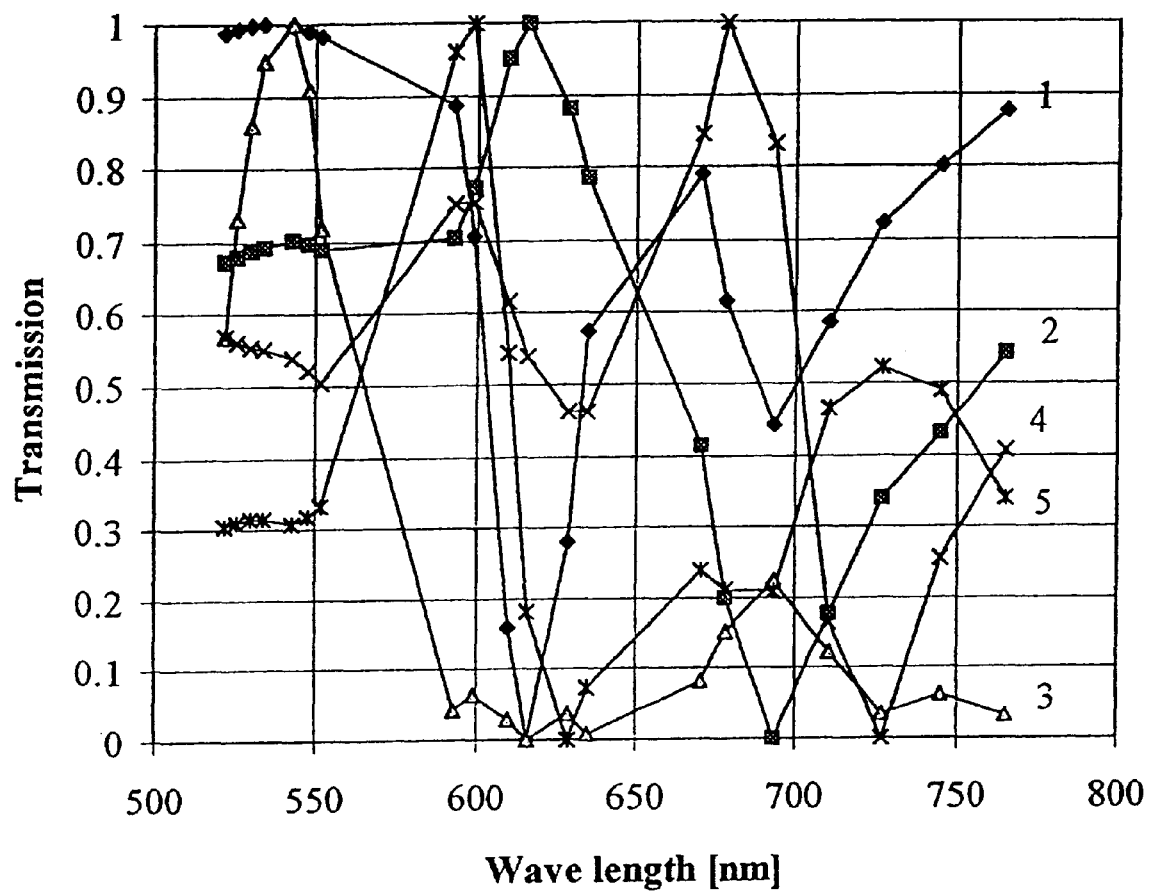
FIG. 9 is a graphic presentation of five decorrelation matched filters as calculated using the data in Tables 4 and 6 and Equation 6.

FIG. 9 graphically depicts five decorrelation matched filters as calculated using the data in tables 4 and 6 and Equation 6.

Thus, by imaging painted chromosomes N+1 times, six in the given example, once for each filter (there are N such filters) and once without any filter and using Equation 8, one can calculate the P N-dimension vector for each pixel in the image. These vectors are then used for classification by employing the pre-prepared reference template, similarly to as described above under classification. As before, for color presentation, pixels attributed to each of the 24 different chromosome types are given a different artificial color to yield a 24 color karyotype.

The above described calculation of the physical filters is presently preferred. Yet, it will be appreciated by one ordinarily skilled in the art that in specific cases different calculations to limit the filters to the full dynamic range of 0–1, or to a segment of the full dynamic range (e.g., 0.1–0.9), are also possible. Furthermore, as each of the PCs shown in the graph of FIG. 6 has at least one positive section and at least one negative section, each of these PCs may be represented by two or more physical filters in which one or some filters represents the positive section(s) of the PC and the other(s) represent the positive magnitude of the negative section(s) of the same PC. It should be further noted that some PCs may have only positive or only negative values. In this case, they may be represented accordingly by one or more filters which represent the positive values of the PC, or, one or more filters which represent the positive magnitude of the negative values of the PC, respectively. In any case, a measurement using these filters can be performed and the P N-dimension vector for each pixel can be determined and used for classification similarly to as described above.

In addition, any of the filters presented in Figure 9, or any other filters differently calculated, for example as described above, may be manufactured as a single filter, alternatively as a subset of few filters, which collectively, when sequentially applied for measurement, yield otherwise substantially identical results. It should thus be noted that when the term decorrelation matched filters is used herein and especially in the claims section below, it refers to all the possible options of calculating and manufacturing these filters, unless otherwise is specifically indicated.

EXAMPLE 7

Decorrelation Matched AOTFs and LCTFs

Tunable filters (TFs), such as acousto-optic tunable filters (AOTFs) and liquid-crystal tunable filters (LCTFs), are solid state electronically tunable spectral bandpass selectors having no moving parts which can be electronically tuned to any particular wavelength, as well known in the art. As such, a tunable filter can be thought of a variable bandpass filter that can be electronically tuned to any wavelength over its range.

A liquid-crystal tunable filter (LCTF) is a solid state electronically tunable spectral bandpass filter typically made of high molecular weight organic substances having a dipole. Tuning LCTF is performed by subjecting the liquid crystal to varying electrical voltages. LCTF is a birefringent filter that uses phase retardation to create constructive and destructive interference. By stacking a number of stages in series, a single bandpass is obtained in a manner similar to that of a multicavity interference filter. LCTF technology was introduced by Cambridge Research & Instrumentation (CRI) Inc. in 1992. The first generation LCTFs produced suffered various limitations as far as bandpass width and shape and transmission of polarized and especially of randomly-polarized light are concerned. However, second generation LCTFs have overcome these problems, enabling transmission of about 100 percent of polarized light, substantially greater than 50 percent of randomly-polarized light, broad bandpass (top and bottom) of variety of shapes in the spectral range of 400 nm to 720 nm. To the development in LCTFs the reader is referred to Clifford Hoyt (1996) Liquid crystals tunable filters clear the way for imaging multiprobe fluorescence. Biomotonics International, 3(4), 49–51. Further information concerning LCTF can be found in for example Hoyt and Benson (1992) Merging spectroscopy and digital imaging enhances cell research. Photonics Spectra 26(11), 92–97; Kopp (1994) Tunable birefringent filters using liquid crystal variable retarders. Proc. SPIE 2265, 192–201; Miller and Hoyt (1995) Multispectral imaging with a liquid crystal tunable filter. Proc. SPIE 2345, 354–365; and Koenig et al. (1994) In-vivo fluorescence detection and imaging of porphyrin-producing bacteria in the human skin and in the oral cavity for diagnosis of acne, caries, and squamous cell carcinoma. Proc. SPIE 2135, 129–138, all are incorporated by reference as if fully set forth herein.

Thus, the physical filters of FIG. 9 can be mimicked by a single LCTF, which can be tuned at different times to mimic a filter of any bandpass of any desirable shape.

An acousto-optic tunable filter (AOTF) is a solid state electronically tunable spectral bandpass filter which can be operated from the ultra violet through the visible and into the infrared regions of the optical spectrum. The AOTF operates on the principle of acousto-optic interaction in an anisotropic medium. In other words the AOTF functions by the interaction of light with traveling acoustic wave through the medium, which creates a periodic modulation of its index of refraction by means of the elasto-optic effect. This modulation acts as a three-dimensional sinusoidal phase grating for light incident upon the crystal, leading to the diffraction of certain wavelengths at an angle from the incident beam radiation. To this end, an acoustic transducer, typically a piezoelectric motor, is bonded to one face of the crystal and an acousto absorber is typically bonded to an opposite face. The transducer converts a high frequency rf (radio frequency) signal into a sinusoidal pressure wave which propagates laterally through the crystal. As a result, the medium operates similar to a grating, wherein incident light is diffracted to its spectral wavelengths, light of varying wavelengths is acquired different angles with respect to the incident light beam when leaving the medium as a throughput. The acoustic absorber at the opposite end of the crystal eliminates acoustic reflections which would corrupt the primary acoustic wave form. The conservation of momentum between the incident and diffracted photon wave vectors and the acoustic wave vector determines the wavelength of the diffracted light passing the medium at a given angle. Thus, without moving the AOTF, one can control the wavelength of light that will pass the medium in a selected angle. Optical tuning, or in other words the wavelength of light which passes the medium in a preselected angle, is achieved by selecting the rf frequency signal.

The use of AOTFs for spectroscopic applications and for spectral imaging applications is not new, see for example U.S. Pat. Nos. 5,216,484 to Chao et al., 5,377,003 to Lewis et al. Further information concerning the operation of AOTFs can be found in for example Wang and Lewis (1996) Acousto-optic tunable filters and their application in spectroscopic imaging and microscopy. In, "Fluorescence Imaging Spectroscopy and Microscopy". Feng, Wang and Brian, Eds. John Wiley and Sons Inc.; Harris et al. (1969) Acousto-optic tunable filters. Journal of the optical society of America, 59, 744–747; Chang (1977) Noncolinear acousto-optic filter with large angular aperture. Applied Physics Letters, 25, 370–372; Eliot et al. (1996) Imaging acousto-optic tunable filter with 0.35-micrometer spatial resolution. Applied Optics, 35, 5220–5226; and in U.S. Pat. Nos. 3,679,288; 3,944,334; 3,944,335; 3,953,107; 4,052,121; 4,342,502 and 5,039,855, all are incorporated by reference.

Traditionally AOTFs were used to generate a varying narrow bandpass. Nevertheless, electronically controlling the acousto wave parameters by for example super imposition (e.g., linear combination) acoustic waves of different wavelengths and/or different amplitudes, by for example employing more than one transducer, enables to select any desired wave pattern that results in passing different intensities of light at variable wavelengths in a preselected angle. Furthermore, by omitting the acousto absorber to allow the presence and therefore superposition of waves reflected from the end face of the crystal can also be used to control passage of different intensities of light at variable wavelengths in the preselected angle. Thus, when driven with multiple closely spaced rfs, the AOTF also provides electronically variable bandpass and shape control. To this effect the reader is referred to Eliot et al. (1996) Imaging acousto-optic tunable filter with 0.35-micrometer spatial resolution. Applied Optics, 35, 5220–5226.

As a result, the physical filters of FIG. 9 can be mimicked by a single AOTF, which can be tuned at different times to mimic a filter of any bandpass having any desirable shape.

As stated above, any of the filters presented in FIG. 9, or any other filters differently calculated, for example as described above in Example 6, may be manufactured as a single filter, alternatively as a subset of few filters, which collectively, when sequentially applied for measurement, yield otherwise substantially identical results. Any such combination of filters may be mimicked by a single tunable filter (LCTF or AOTF) which can be tuned at a different bandpass and shape to sequentially mimic any of the filters. Thus, when the term decorrelation matched filters is used herein and especially in the claims section below, it refers to these options as well.

It will be appreciated that by using tunable filters such as AOTF and LCTF, a single filter is required for measurement, the tunable filter is tuned to change its spectral characteristics in a manner that sequentially follows any desired characteristics. Thus for measurement of in situ hybridized chromosomes according to a given experimental procedure, tuning information is selected such that the tunable filter sequentially mimics decorrelation matched filters. This, however implies that the measurement involves no moving parts as it is electronically controlled.

EXAMPLE 8

A Spectral Decorrelation Measurement Apparatus Based on Decorrelation Matched Optical Filtersfor Chromosome Analysis As described above, for a given experimental protocol, e.g., given types of fluorophores and/or combinations thereof, a set of N (e.g., three to five) decorrelation matched filters can be calculated and manufactured. These filters can be used for fast collection of decorrelated projection of each pixel spectrum in a tield of view onto a number of orthogonal PCs, provided that the observed object is treated according to the experimental protocol employed for calculating the transmittance function of the filters. These N values, collectively form an N-dimension vector for each pixel. Each of these vectors is then compared to reference vectors forming a reference template for classification as described above, and, based on this comparison, each pixel is attributed to a chromosome type and for presentation given a specifying artificial color.

Figure 10:
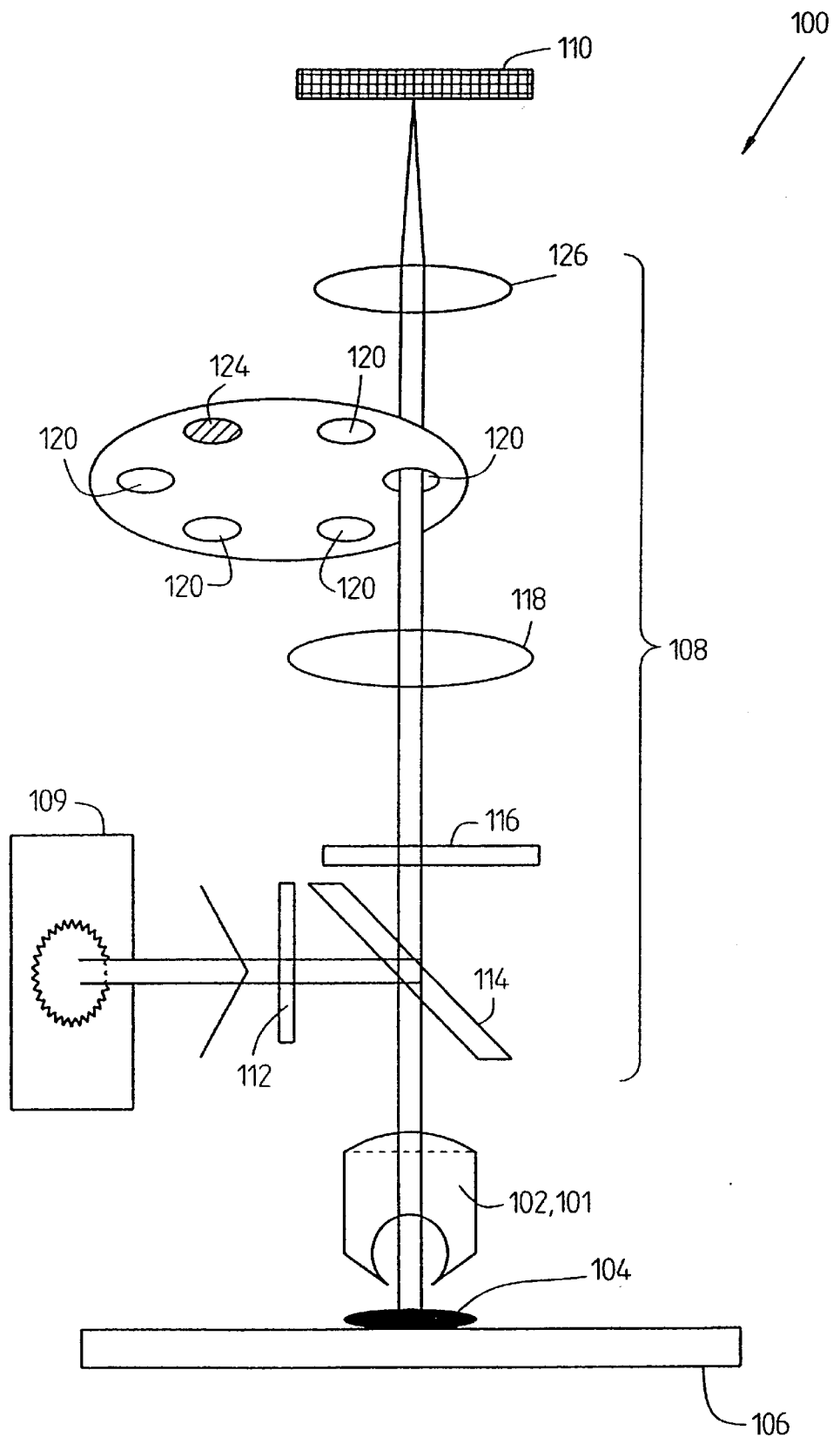
FIG. 10 is a schematic depiction of a filter wheel including spectral decorrelation measurement apparatus suitable for chromosome analysis.

With reference now to FIG. 10. For ease of measurement, the N decorrelation matched filters are placed in an apparatus referred hereinbelow as a spectral decorrelation measurement apparatus or apparatus 100. Apparatus 100 is connected to a microscope 101, which is indicated by its objective lens 102. A sample of in situ painted chromosomes 104 to be analyzed is placed under microscope 101, on a supporting plane 106. Apparatus 100 further includes an optical system 108, which is for transmitting excitation light from light source 109 to sample 104 and emission light from sample 104 onto a detector 110, typically a two dimensional CCD array.

In a preferred embodiment, optical system 108 includes an excitation filter 112, which is placed in the path of light emitted from light source 109. Excitation filter 112 is capable of transmitting light in the range required for excitation of the fluorophores in sample 104, e.g., in the ultraviolet and blue ranges, and of blocking light in the range of fluorescent emission. Optical system 108 further includes a dichroic filter 114, typically a triple dichroic filter, for directing exiting light from filter 112 to sample 104 and emission light from sample 104 to detector 110. Preferably, optical system 108 further includes a barrier filter 116 for blocking any residual photons which are not in the spectral range of the emitted fluorescence. Depending on the type of microscope 101 employed, optical system 108 may further include a collimating lens 118 to ensure full collimation of the light. However, as well known in the art, some microscopes include a collimating lens themselves. In these cases collimating lens 118 may be discarded.

Optical system 108 further includes N (N is an integer greater than two, preferably N is in the range of 3–5) decorrelating matched filters 120, live of which are shown in FIG. 10, peripherally arranged on a rotatable filter carrying element 122, such as a filter wheel. Each of decorrelating matched filters 120 is designed as described hereinabove under Example 6. Rotatable filter carrying element 122 also includes one position 124 through which light passes undisturbed. The number N of decorrelating matched filters 120 may vary as described above and is determined by the number of eigenvalues or PCs employed to construct the reference vector for each of the chromosomes, or, in other words, the reference template.

Optical system 108 further includes a focusing lens 126 for focusing light after passage through rotatable filter carrying element 122 onto detector 110.

The operation of apparatus 100 is as follows. Decorrelating matched filters 120 of rotatable filter carrying element 122 are kept successively in the light beam while detector 110 builds an images for each. That is to say that detector 110 builds an image with first filter 120, then rotatable filter carrying element 122 rotates to present another filter 120, and detector 110 starts building a new image in synchronization, and so on until one image for each filter 120 has been measured. One additional image is formed while position 124 through which light passes undisturbed is positioned in the path of light.

Using the data thus collected, Equation 8 above and the data in tables 4 and 6, the coordinates of the P N-dimension vector for each pixel are calculated in the N-dimensional space of the N PCs. These coordinates are then used for classification by employing the pre-prepared reference template, similarly to as described above under classification. As before, for color presentation, pixels attributed to each of the 24 different chromosome types are given a different artificial color to yield a 24 color karyotype.

EXAMPLE 9

A Spectral Decorrelation Measurement Apparatus Based on Decorrelation Matched AOTFs and LCTFs for Chromosome Analysis As described above in Example 8, for a given experimental protocol, e.g., given types of fluorophores and/or combinations thereof, a set of N (e.g., three to decorrelation matched filters can be calculated and implemented by electronically tuning a tunable filter such as an AOTF or LCTF. Any of these filters can be used for fast collection of decorrelated projection of each pixel spectrum in a field of view onto a number of orthogonal PCs, provided that the observed object is treated according to the experimental protocol employed for calculating the transmittance function of the filters as implemented by tuning. These N values, collectively form an N-dimension vector for each pixel. Each of these vectors is then compared to reference vectors forming a reference template for classification as described above, and, based on this comparison, each pixel is attributed to a chromosome type and for presentation given a specifying artificial color.

Figure 11:
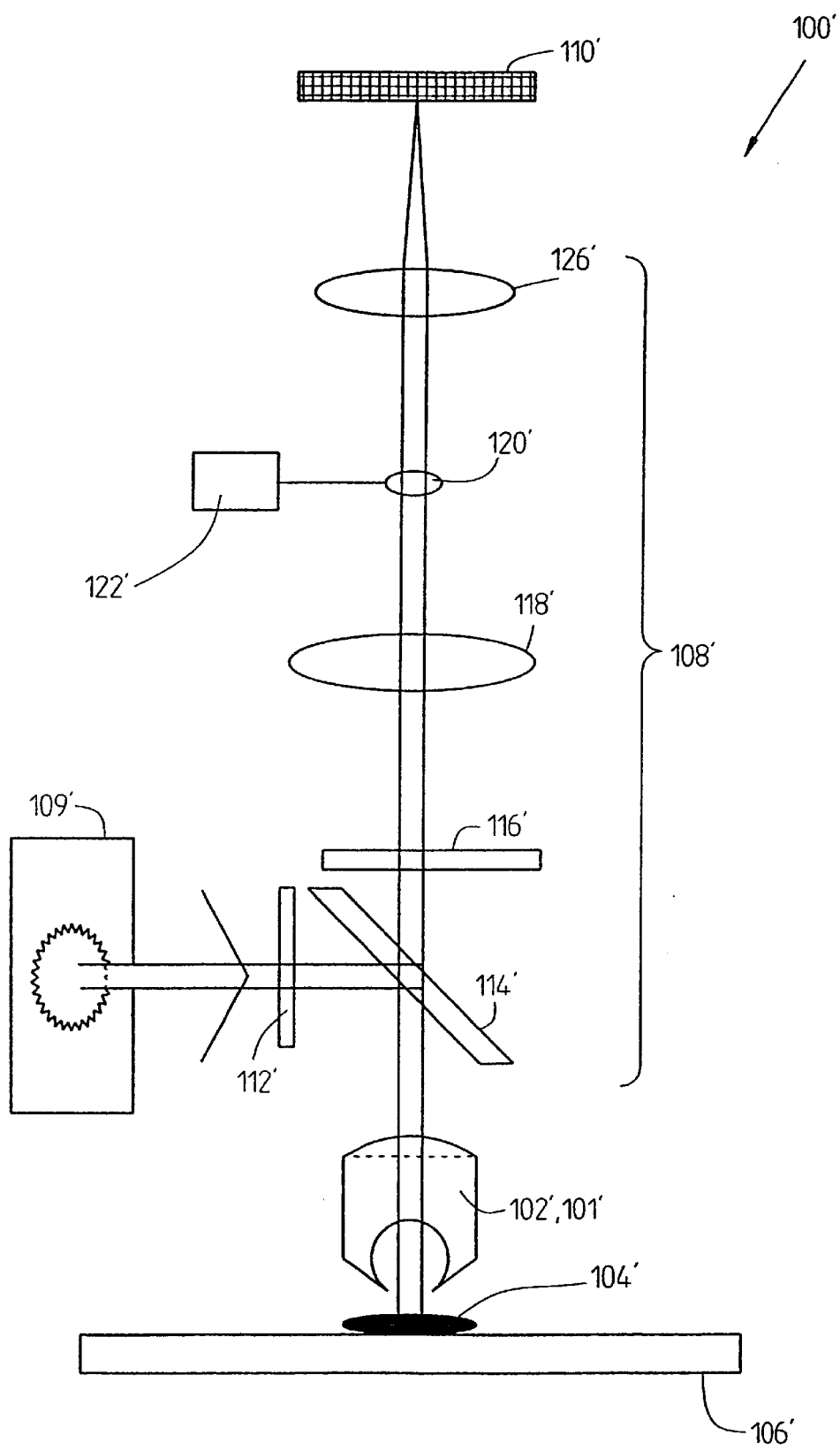
FIG. 11 is a schematic depiction of a tunable filter including spectral decorrelation measurement apparatus suitable for chromosome analysis.

With reference now to FIG. 11. For ease of measurement, a tunable filter to serve as the decorrelation matched filters is placed in an apparatus which is referred to hereinbelow as a spectral decorrelation measurement apparatus, or apparatus 100'. Apparatus 100' is connected to a microscope 101', which is indicated by its objective lens 102'. A sample of in situ painted chromosomes 104' to be analyzed is placed under microscope 101', on a supporting plane 106'. Apparatus 100' further includes an optical system 108', which is for transmitting excitation light from light source 109' to sample 104' and emission light from sample 104' onto a detector 110', typically a two dimensional CCD array.

In a preferred embodiment, optical system 108' includes an excitation filter 112', which is placed in the path of light emitted from light source 109'. Excitation filter 112' is capable of transmitting light in the range required for excitation of the fluorophores in sample 104', e.g., in the ultraviolet and blue ranges, and of blocking light in the range of fluorescent emission. Optical system 108' further includes a dichroic filter 114', typically a triple dichroic filter, for directing exiting light from filter 112' to sample 104' and emission light from sample 104' to detector 110'. Preferably, optical system 108' further includes a barrier filter 116' for blocking any residual photons which are not in the spectral range of the emitted fluorescence. Depending on the type of microscope 101' employed, optical system 108' may further include a collimating lens 118' to ensure full collimation of the light. However, as well known in the art, some microscopes include a collimating lens themselves. In these cases collimating lens 118' may be discarded.

Optical system 108' further includes a tunable filter 120' and a tuning device 122'. Tuning device 122' is for sequentially tuning filter 120' according to precalculated tuning information to sequentially mimic N (N is an integer greater than two, preferably N is in the range of 3–5) decorrelating matched filters as described above under Example 7. Device 122' preferably also includes tuning information to transform filter 120' into a transparent optical element through which light passes undisturbed. The number N of mimicked decorrelating matched filters may vary as described above and is determined by the number of eigenvalues or PCs employed to construct the reference vector for each of the chromosomes, or, in other words, the reference template.

Optical system 108' further includes a focusing lens 126' for focusing light after passage through filter 120' onto detector 110'.

The operation of apparatus 100 is as follows. Tunable filter 120' is sequentially tuned by tuning device 122' according to a precalculated set of information, as described above, to sequentially mimic the N decorrelating matched filters, such that at selected times a different decorrelating matched filter is mimicked, while detector 110' builds an images for each until one image for each mimic has been measured. One additional image is formed while filter 120' is tuned such that light passes therethrough is undisturbed, or without filter 120' altogether.

Using the data thus collected, Equation 8 above and the data in Tables 4 and 6, the coordinates of the P N-dimension vector for each pixel are calculated in the N-dimensional space of the N PCs. These coordinates are then used for classification by employing the pre-prepared reference template, similarly to as described above under classification. As before, for color presentation, pixels attributed to each of the 24 different chromosome types are given a different artificial color to yield a 24 color karyotype.

The apparatus of the present example has advantages over the apparatus of Example 9 in two respects. First, the apparatus according to this example has no moving parts. Second, the apparatus according to this Example is less "dedicated". That is to say, should a different experimental procedure employed for chromosome painting or banding, a new set of information is calculated to permit the tunable filter to mimic a different set of decorrelation matched filters, suitable for data collection from the chromosomes according to the methods ol the present invention and as detailed above. The operation of the apparatus of the present Example is highly suitable for computer control, which can control the operation of tuning device 122'. Therefore, a single apparatus can be made suitable for classification and analysis of painted and banded chromosomes painted or banded by various experimental procedures, simply by employing a matching software which includes an appropriate set of information for controlling the operation of device 122', and therefore of tunable filter 120'.

Turning back to remote sensing, a field of view is similar to the chromosomes sample described above. It includes scenes, each of which is spectrally different from the other just like the chromosomes when painted as described. Therefore, the principles of chromosome classification as exemplified above, apply also to remote sensing of scenes in a field of view, with the provision that each of the scenes differs from the other scenes in some spectral characteristics. This, however, is the case as described in the background section above. The main differences between the measurement of metaphase chromosomes and remote scenes can be summarized as follows:

TABLE 7

| Item | Chromosomes | Remote scenes |
| --- | --- | --- |
| Optical configuration | Microscopic, covered with one SPECTRACUBE ™ system | Telescopic, covered with several systems |
| Spectral range | 0.4 to 0.8 $\mu$m | 0.3 to 14 $\mu$m |
| Optical elements | Suitable for visible radiation | Suitable for the specific range in each system |
| Type of radiation | Fluorescence | Sun reflection, thermal self-emission or luminescence |
| Sample preparation | Hybridization and labeling | None - natural spectral signatures |

The main difference from the point of view of analyzing the spectral cube data is that in the case of chromosomes there is a definite and known number of objects (24 in human male) to detect and recognize over an almost non-emitting background (because we work in highly specific fluorescence labeling), and therefore each pixel must be classified in one of a discrete set of classes. In the case of remote sensing the scenes to detect and recognize are usually surrounded by a multitude of other scenes from which they have to be distinguished (i.e., nonzero background); in addition, the status of fields, crops health, vegetation stress, lakes pollution, algae content, sea and streams temperature, rock types, soil temperature and humidity, etc., can usually be characterized by a continuum of values (nondiscrete set of classes). However, carefully selecting the reference template would enable to resolve the principal components which best described the spectral signature characterizing each of the analyzed scenes.

EXAMPLE 10

A Spectral Decorrelation Measurement Apparatus Based on Decorrelation Matched Optical Filters for Remote Sensing As is derived from the above examples, a set of N decorrelation matched filters can be calculated and manufactured for remote sensing of scenes in a field of view. These filters can be used for fast collection ot decorrelated projection of each pixel spectrum in a field of view onto a number of orthogonal PCs. These N values, collectively form an N-dimension vector for each pixel. Each of these vectors is then compared to reference vectors forming a reference template for classification, and, based on this comparison, each pixel is attributed to a specific scene, and for presentation, is given a specifying artificial color.

Figure 12:
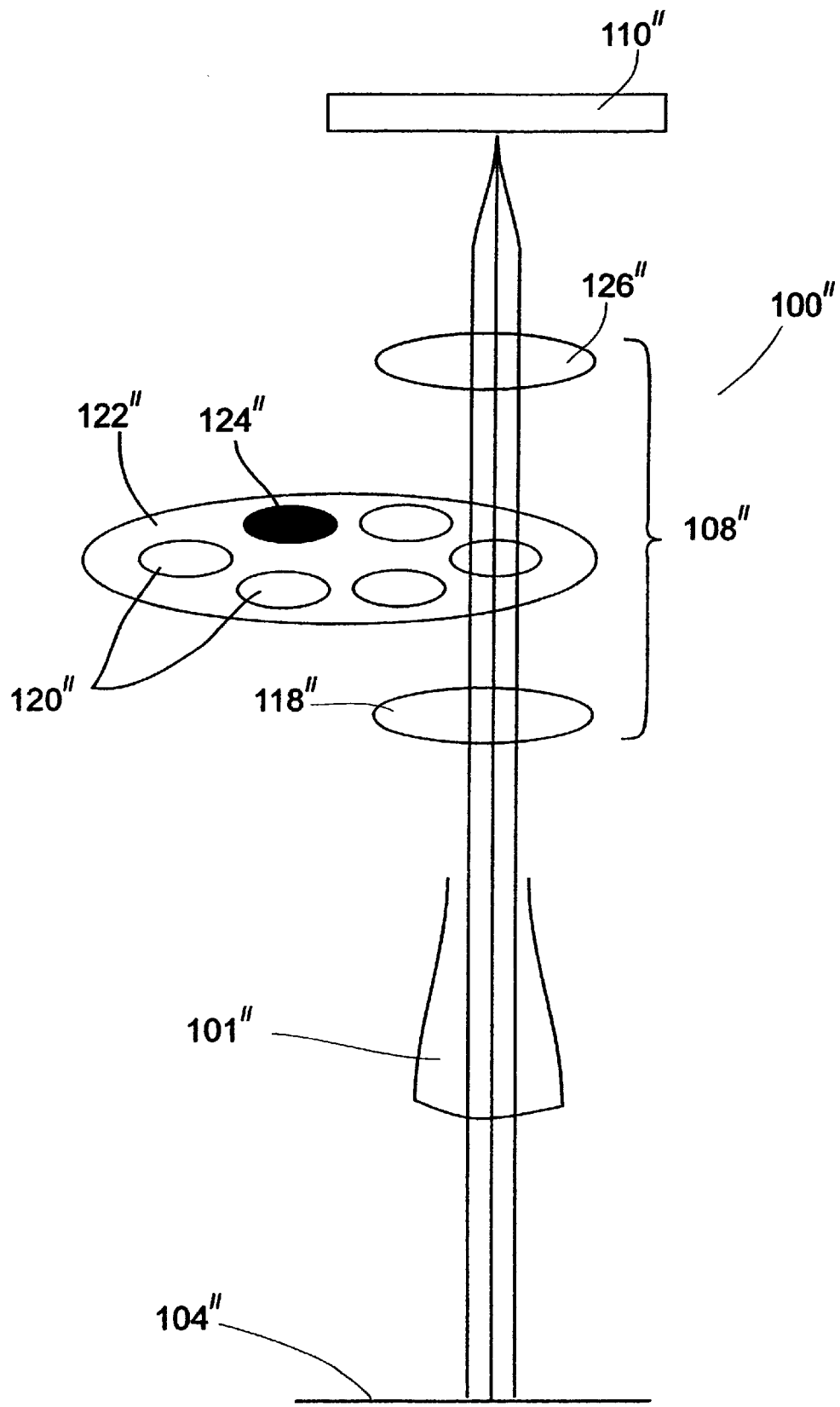
FIG. 12 is a schematic depiction of a filter wheel including spectral decorrelation measurement apparatus suitable for remote sensing.

With reference now to FIG. 12. For ease of measurement, the N decorrelation matched filters are placed in an apparatus referred hereinbelow as a spectral decorrelation measurement apparatus or apparatus 100". Apparatus 100" is connected to a telescope 101". A remote field of view 104" to be analyzed is viewed via telescope 101". Apparatus 100" further includes an optical system 108", which is for transmitting radiation from field 104" onto a detector 110", typically a two dimensional CCD array.

Depending on the type of telescope 101" employed, optical system 108" may further include a collimating lens 118" to ensure full collimation of the light. However, as well known in the art, some telescopes include a collimating lens themselves. In these cases collimating lens 118" may be discarded.

Optical system 108" further includes N (N is an integer greater than two, preferably N is in the range of 3–5) decorrelating matched filters 120", five of which are shown in FIG. 12, peripherally arranged on a rotatable filter carrying element 122", such as a filter wheel. Each of decorrelating matched filters 120" is designed as described. Rotatable filter carrying element 122" also includes one position 124" through which light passes undisturbed. The number N of decorrelating matched filters 120"0 may vary and is determined by the number of eigenvalues or PCs employed to construct the reference vector for each of the scenes in the field of view.

Optical system 108" further includes a focusing lens 126" for focusing light after passage through rotatable filter carrying element 122" onto detector 110".

The filters' 102" positions are preferably selected to be on the collimated section of the beam, but not necessarily: they can also be between the focusing lens and the detector (in this case, near the detector the beam size is smallest, and therefore this position is preferred).

The operation of apparatus 100" is as follows. Decorrelating matched filters 120" of rotatable filter carrying element 122" are kept successively in the radiation beam while detector 110" builds an images for each. That is to say that detector 110" builds an image with first filter 120", then rotatable filter carrying element 122" rotates to present another filter 120", and detector 110" starts building a new image in synchronization, and so on until one image for each filter 120" has been measured. One additional image is formed while position 124" through which light passes undisturbed is positioned in the path of light.

Using the data thus collected, Equation 8 above and a suitable look-up table, the coordinates of the P N-dimension vector for each pixel are calculated in the N-dimensional space of the N PCs. These coordinates are then used for classification by employing the pre-prepared reference template. For color presentation, pixels attributed to each scene in the field of view are given a different artificial color to distinct among the scenes.

From the above descriptions, it is clear that the filter wheel may be replaced by a tunable filter and a suitable tuning device.

While the invention has been described with respect to a limited number of embodiments, it will be appreciated that many variations, modifications and other applications of the invention may be made.

What is claimed is:

1. A method for preparing a reference template for classification of remote scenes comprising the steps of:
    (a) classifying a set of reference scenes via a conventional classification technique for obtaining a set of preclassified scenes;
    (b) using a spectral imager for measuring a spectral cube of said preclassified referenced scenes;

(c) employing a decorrelation statistical method for extracting said spectral cube for decorrelated spectral data characterizing said reference scenes; and (d) using at least a part of said decorrelated spectral data for the preparation of the reference template for remote scenes classification.

2. The method for preparing a reference template for classification of remote scenes as in claim 1, wherein said spectral imager includes an element selected from the group consisting of a dispersion element, a filter, a tunable filter and an interferometer.

3. The method for preparing a reference template for classification of remote scenes as in claim 1, wherein said decorrelation statistical method is selected from the group consisting of principal component analysis, canonical variable analysis and singular value decomposition.

4. The method for preparing a reference template for classification of remote scenes as in claim 3, wherein said principal component analysis includes expressing each of said scenes as linear combinations of N eigenvectors.

5. The method for preparing a reference template for classification of remote scenes as in claim 4, wherein N is an integer greater than two.

6. The method for preparing a reference template for classification of remote scenes as in claim 4, wherein N is an integer greater than two and smaller than eight.

7. The method for preparing a reference template for classification of remote scenes as in claim 3, wherein said principal component analysis includes the steps of:

(a) selecting k spectral slices for said spectral cube of said reference scenes;

(b) calculating an average spectrum for each of said reference scenes;

(c) stretching each of said average spectra for obtaining a stretched average spectrum for each of said reference scenes;

(d) averaging said stretched average spectra for each of said reference scenes, for obtaining an ensemble average spectrum for each of said reference scenes;

(e) calculating a k dimension eigen system for said ensemble average spectra and extracting N eigenvectors;

(f) using said N eigenvectors for defining an N-dimension vector for each of said reference scenes; and (g) using said N-dimension vectors for preparing the reference template for the remote scenes classification.

8. The method for preparing a reference template for classification of remote scenes as in claim 7, wherein k is an integer greater than nine.

9. The method for preparing a reference template for classification of remote scenes as in claim 7, wherein N is an integer greater than two.

10. The method for preparing a reference template for classification of remote scenes as in claim 7, wherein said principal component analysis further includes the step of:

(h) performing a spatial averaging procedure over all spectral slices.

11. A method for remote scenes classification comprising the steps of:

(a) preparing a reference template for classification of the remote scenes via:

(i) classifying a set of reference scenes via a conventional classification technique for obtaining a set of preclassified reference scenes;

(ii) using a first spectral imager for measuring a spectral cube of said preclassified reference scenes;

(iii) employing a principal component analysis for extracting said spectral cube for decorrelated spectral data characterizing said reference scenes; and (vi) using at least a part of said decorrelated spectral data for the preparation of the reference template for remote scenes classification;

(b) using a second spectral imager for measuring a spectral cube of analyzed remote scenes, such that a spectrum of each pixel in said remote scenes is obtained;

(c) employing a decorrelation statistical method for extracting decorrelated spectral data characterizing said pixels; and (d) comparing at least a part of said decorrelated spectral data extracted from said pixels of the remote scenes with said reference template.

12. A method for remote scenes classification comprising the steps of:

(a) preparing a reference template for classification of remote scenes via:

(i) classifying a set of reference scenes via a conventional classification technique for obtaining a set of preclassified reference scenes;

(ii) using a first spectral imager for measuring a spectral cube of said preclassified reference scenes;

(iii) employing a decorrelation statistical method for extracting said spectral cube for decorrelated spectral data characterizing said reference scenes; and (iv) using at least a part of said decorrelated spectral data for the preparation of the reference template for the remote scenes classification;

(b) using a second spectral imager for measuring a spectral cube of analyzed remote scenes, such that a spectrum of each pixel in said remote scenes is obtained;

(c) projecting said spectrum of each of said pixels onto said decorrelated spectral data for obtaining a projected spectrum for each of said pixels; and (d) comparing said projected spectra with said reference template.

13. The method for remote scenes classification as in claim 11, further comprising the step of:

(f) according to said comparison, attributing each pixel an artificial color.

14. The method for remote scenes classification as in claim 11, wherein said spectral imager includes an element selected from the group consisting of a dispersion element, a filter and an interfcrometer.

15. The method for remote scenes classification as in claim 11, wherein said decorrelation statistical method is selected from the group consisting of principal component analysis, canonical variable analysis and singular value decomposition.

16. The method for remote scenes classification as in claim 15, wherein said principal component analysis includes expressing each of said analyzed scenes as linear combinations of N eigenvectors.

17. A method for remote scenes classification comprising the steps of:

(a) preparing a reference template for classification of remote scenes via:

(i) classifying a set of reference scenes via a conventional classification technique for obtaining a set of preclassified reference scenes;

(ii) using a first spectral imager for measuring a spectral cube of said preclassified reference scenes;

(iii) employing a principal component analysis for extracting said spectral cube for decorrelated spectral data characterizing said reference scenes via:
  (a) selecting k spectral slices for said spectral cube of said reference scenes;
  (b) calculating an average spectrum for each of said reference scenes;
  (c) stretching said average spectra for obtaining a stretched average spectrum for each of said reference scenes;
  (d) averaging said stretched average spectra for each of said reference scenes for obtaining an ensemble average spectrum for each of said reference scenes;
  (e) calculating a k dimension eigen system for said ensemble average spectra and extracting N eigenvectors;
  (f) using said N eigenvectors for defining an N-dimension vector for each of said reference scenes; and
  (g) using said N-dimension vectors for preparing said reference template for the remote scenes classification;
(b) using a second spectral imager for measuring a spectral cube of the remote scenes, such that a spectrum of each pixel in the remote scenes is obtained;
(c) projecting said spectrum of each of said pixels into said N eigenvectors for obtaining a projected N dimension vector for each of said pixels; and
(d) correlating each of said projected N dimension vectors with said reference template.

18. The method for remote scenes classification as in claim 17, the method further comprising the step of performing a spatial averaging procedure on all spectral slices.

19. A method of calculating decorrelation matched filters for remote scenes classification, the decorrelation matched filters being for extracting decorrelated spectral data from the remote scenes, the method comprising the step of:
(a) obtaining decorrelated spectral data characterizing a set of reference scenes via:
  (i) classifying said set of reference scenes via a conventional classification technique for obtaining a set of preclassified reference scenes;
  (ii) using a first spectral imager for measuring a spectral cube of said preclassified reference scenes; and
  (iii) employing a decorrelation statistical method for extracting said spectral cube for decorrelated spectral data characterizing said reference scenes; and
(b) mathematically manipulating at least a part of said decorrelated spectral data for obtaining a mathematical description of the decorrelation matched filters.

20. The method of calculating decorrelation matched filters for remote scenes classification as in claim 19, wherein said decorrelated spectral data is obtained using a principal component analysis, which includes expressing each of said reference scenes by a linear combination of N eigenvectors.

21. A set of decorrelation matched filters for remote scenes classification, the decorrelation matched filters being for extracting decorrelated spectral data from the remote scenes, the set comprising physical filters having shapes, said shapes following a mathematical description, said mathematical description being obtainable by:
(a) obtaining decorrelated spectral data characterizing a set of reference scenes via:
  (i) classifying said set of reference scenes via a conventional classification technique for obtaining a set of preclassified reference scenes;
  (ii) using a first spectral imager for measuring a spectral cube of said preclassified reference scenes; and
  (iii) employing a decorrelation statistical method for extracting said spectral cube for decorrelated spectral data characterizing said reference scenes; and
(b) mathematically manipulating at least a part of said decorrelated spectral data for obtaining said mathematical description of the decorrelation matched filters.

22. A method of tuning a tunable filter for remote scenes classification, the method renders the tunable filter to mimic a set of decorrelation matched filters, and is for extracting decorrelated spectral data from the remote scenes, the method comprising the steps of:
(a) obtaining decorrelated spectral data characterizing a set of reference scenes via:
  (i) classifying said set of reference scenes via a conventional classification technique for obtaining a set of preclassified reference scenes;
  (ii) using a first spectral imager for measuring a spectral cube ol said preclassified reference scenes; and
  (iii) employing a decorrelation statistical method for extracting said spectral cube for decorrelated spectral data characterizing said reference scenes;
(b) mathematically manipulating at least a part of said decorrelated spectral data for obtaining a mathematical description describing the set of decorrelation matched filters; and
(c) sequentially tuning the tunable filter according to said mathematical description.

23. The method of tuning a tunable filter for remote scenes classification as in claim 22, wherein said tunable filter is selected from the group consisting of AOTF and LCTF.

24. A method for remote scenes classification comprising the steps of:
(a) preparing a reference template for classification of the remote scenes via:
  (i) classifying a set of reference scenes via a conventional classification technique for obtaining a set of preclassified reference scenes;
  (ii) using a first spectral imager for measuring a spectral cube of said preclassified reference scenes;
  (iii) employing a decorrelation statistical method lor extracting said spectral cube for decorrelated spectral data characterizing said reference scenes; and
  (iv) using at least a part of said decorrelated spectral data for the preparation of the reference template for the remote scenes classification;
(b) calculating a mathematical description of decorrelation matched filters for classification of the remote scenes employing said reference template, said calculation being by mathematically manipulating at least a part of said decorrelated spectral data;
(c) using said mathematical description of said decorrelation matched filters for manufacturing said decorrelation matched filters;
(d) using said decorrelation matched filters for extracting decorrelated spectral data from each pixel of the remote scenes; and
(e) comparing said decorrelated spectral data extracted from each pixel of the remote scenes with the reference template.

25. The method for remote scenes classification as in claim 24, further comprising the step of:
(f) attributing each pixel an artificial color according to said comparison.

26. The method for remote scenes classification as in claim 24, wherein said decorrelation statistical method is selected from the group consisting of principal component analysis, canonical variable analysis and singular value decomposition.

27. The method for remote scenes classification as in claim 26, wherein said principal component analysis includes expressing each of said reference scenes as linear combinations of N eigenvectors.

28. A method for remote scenes classification comprising the steps of:
 (a) providing a set of decorrelation matched filters for the remote scenes classification, the decorrelation matched filters being for extracting decorrelated spectral data from the remote scenes, the set including physical filters having shapes, said shapes following a mathematical description, said mathematical description being achieved by:
  (i) preparing a reference template for classification of remote scenes via:
   (a) classifying a set of reference scenes via a conventional classification technique for obtaining a set of preclassified reference scenes;
   (b) using a first spectral imager for measuring a spectral cube of said preclassified reference scenes;
   (c) employing a decorrelation statistical method for extracting said spectral cube for decorrelated spectral data characterizing said reference scenes; and
   (d) using at least a part of said decorrelated spectral data for the preparation of the reference template for the remote scenes classification; and
  (ii) mathematically manipulating at least a part of said decorrelated spectral data for obtaining said mathematical description of said decorrelation matched filters;
 (b) using said decorrelation matched filters for extracting decorrelated spectral data from each pixel of the remote scenes; and
 (c) comparing said decorrelated spectral data extracted from each pixel of the remote scenes with the reference template.

29. The method for remote scenes classification as in claim 28, further comprising the step of:
 (d) according to said comparison, attributing each pixel an artificial color.

30. The method for remote scenes classification as in claim 28, wherein said decorrelation statistical method is selected from the group consisting of principal component analysis, canonical variable analysis and singular value decomposition.

31. The method for remote scenes classification as in claim 30, wherein said principal component analysis includes expressing each of said reference scenes as linear combinations of N eigenvectors.

32. A method for remote scenes classification comprising the steps of:
 (a) providing a tunable filter and tuning information for tuning said tunable filter so as to mimic a set of decorrelation matched filters, said tunable filter being for extracting decorrelated spectral data from the remote scenes, said tuning information being achieved by:
  (i) preparing a reference template for classification of remote scenes via:
   (a) classifying a set of reference scenes via a conventional classification technique for obtaining a set of preclassified reference scenes;
   (b) using a first spectral imager for measuring a spectral cube of said preclassified reference scenes;
   (c) employing a decorrelation statistical method for extracting said spectral cube for decorrelated spectral data characterizing said reference scenes; and
   (d) using at least a part of said decorrelated spectral data for the preparation of the reference template for the remote scenes classification;
  (ii) mathematically manipulating at least a part of said decorrelated spectral data for obtaining said tuning information, which is a mathematical description describing said set of decorrelation matched filters; and
 (b) using said information for sequentially tuning said tunable filter for extracting decorrelated spectral data from each pixel of the remote scenes; and
 (c) comparing said decorrelated spectral data extracted from each pixel of the remote scenes with the reference template.

33. A spectral decorrelation measurement apparatus for remote scenes classification by extracting decorrelated spectral data from the remote scenes, the apparatus is connected to a telescope used to view the remote scenes, said apparatus comprising:
 (a) a detector; and
 (b) an optical system for transmitting electromagnetic radiation from the remote scenes onto said detector, said optical system including a set of decorrelating matched filters, said decorrelation matched filters being for extracting decorrelated spectral data from the remote scenes, said filters of said set of decorrelation matched filters having shapes, said shapes following a mathematical description, said mathematical description being calculated by:
  (i) obtaining decorrelated spectral data characterizing a set of reference scenes via:
   (a) classifying said set of reference scenes via a conventional classification technique for obtaining a set of preclassified reference scenes;
   (b) using a first spectral imager for measuring a spectral cube of said preclassified reference scenes; and
   (c) employing a decorrelation statistical method flor extracting said spectral cube for decorrelated spectral data characterizing said reference scenes; and
  (ii) mathematically manipulating at least a part of said decorrelated spectral data for obtaining said mathematical description of the decorrelation matched filters.

34. The spectral decorrelation measurement apparatus for remote scenes classification as in claim 33, wherein said optical system further includes a collimating lens for collimating radiation reaching any of said decorrelating matched filters.

35. The spectral decorrelation measurement apparatus for remote scenes classification as in claim 33, wherein said decorrelation matched filters are arranged on a rotatable filter carrying element.

36. A spectral decorrelation measurement apparatus for remote scenes classification by extracting decorrelated spectral data from the remote scenes, the apparatus is connected to a telescope used to view the remote scenes, said apparatus comprising:

(a) a detector; and
(b) an optical system for transmitting electromagnetic radiation from the remote scenes onto said detector, said optical system including a tunable filter and a tuning device, said tuning device being for tuning said tunable filter, so that said tunable filter sequentially mimics a set of decorrelating matched filters, said decorrelation matched filters mimicked by said tunable filter being for extracting decorrelated spectral data from the remote scenes, said tuning of said tunable filter being calculated according to a mathematical description, said mathematical description being calculated by:
  (i) obtaining decorrelated spectral data characterizing a set of reference scenes via:
    (a) classifying said set of reference scenes via a conventional classification technique for obtaining a set of preclassified reference scenes;
    (b) using a first spectral imager for measuring a spectral cube of said preclassified reference scenes; and
    (c) employing a decorrelation statistical method for extracting said spectral cube for said spectral cube for decorrelated spectral data characterizing said reference scenes; and
  (ii) mathematically manipulating at least a part of said decorrelated spectral data for obtaining said mathematical description of said mimicked decorrelation matched filters.

* * * * *